United States Patent
Golijanin et al.

(10) Patent No.: US 10,434,190 B2
(45) Date of Patent: Oct. 8, 2019

(54) PRE-AND-INTRA-OPERATIVE LOCALIZATION OF PENILE SENTINEL NODES

(71) Applicant: NOVADAQ TECHNOLOGIES ULC, Burnaby (CA)

(72) Inventors: Dragan Golijanin, Rochester, NY (US); Lukasz Brzozowski, Toronto (CA); Ronald Wood, Rochester, NY (US)

(73) Assignee: NOVADAQ TECHNOLOGIES ULC, Burnaby (CA)

( * ) Notice: Subject to any disclaimer, the term of this patent is extended or adjusted under 35 U.S.C. 154(b) by 0 days.

(21) Appl. No.: 15/610,102

(22) Filed: May 31, 2017

(65) Prior Publication Data

US 2018/0104362 A1  Apr. 19, 2018

Related U.S. Application Data

(63) Continuation of application No. 11/851,312, filed on Sep. 6, 2007, now abandoned.

(60) Provisional application No. 60/843,175, filed on Sep. 7, 2006.

(51) Int. Cl.
| | | |
|---|---|---|
| A61B 10/00 | (2006.01) | |
| A61B 5/00 | (2006.01) | |
| A61B 8/00 | (2006.01) | |
| A61K 49/00 | (2006.01) | |

(52) U.S. Cl.
CPC ................................. *A61K 49/0034* (2013.01)

(58) Field of Classification Search
CPC ............... A61K 49/00; A61K 49/0034; A61K 2121/00; A61K 2300/00; A61K 2123/00
USPC .......................... 424/1.11, 1.65, 9.1, 9.2, 9.6
See application file for complete search history.

(56) References Cited

U.S. PATENT DOCUMENTS

| | | | |
|---|---|---|---|
| 4,109,647 A | 8/1978 | Stern et al. | |
| 4,162,405 A | 7/1979 | Chance et al. | |
| 4,200,801 A | 4/1980 | Schuresko | |
| 4,263,916 A | 4/1981 | Brooks et al. | |
| 4,394,199 A | 7/1983 | Barnhard, IV et al. | |
| 4,473,841 A | 9/1984 | Murakoshi et al. | |
| 4,532,918 A | 8/1985 | Wheeler | |
| 4,541,438 A | 9/1985 | Parker et al. | |
| 4,556,057 A | 12/1985 | Hiruma et al. | |
| 4,619,249 A | 10/1986 | Landry | |
| 4,718,417 A | 1/1988 | Kittrell et al. | |
| 4,719,508 A | 1/1988 | Sasaki et al. | |
| 4,768,513 A | 9/1988 | Suzuki | |
| 4,773,097 A | 9/1988 | Suzaki et al. | |
| 4,774,568 A | 9/1988 | Matsuo | |
| 4,786,813 A | 11/1988 | Svanberg et al. | |
| 4,805,597 A | 2/1989 | Iwakoshi | |
| 4,815,848 A | 3/1989 | Hadeishi | |
| 4,821,117 A | 4/1989 | Sekiguchi | |
| 4,827,908 A | 5/1989 | Matsuo | |
| 4,852,579 A | 8/1989 | Gilstad et al. | |
| 4,858,001 A | 8/1989 | Milbank et al. | |
| 4,860,731 A | 8/1989 | Matsuura | |
| 4,867,137 A | 9/1989 | Takahashi | |
| 4,868,647 A | 9/1989 | Uehara et al. | |
| 4,900,934 A | 2/1990 | Peeters et al. | |
| 4,930,516 A | 6/1990 | Alfano et al. | |
| 4,938,205 A | 6/1990 | Nudelman | |
| 4,957,114 A | 9/1990 | Zeng et al. | |
| 4,993,404 A | 2/1991 | Lane | |
| 4,995,396 A | 2/1991 | Inaba et al. | |
| 4,995,398 A | 2/1991 | Turnidge | |
| 4,998,972 A | 3/1991 | Chin et al. | |
| 5,003,977 A | 4/1991 | Suzuki et al. | |
| 5,042,494 A | 8/1991 | Alfano | |
| 5,071,417 A | 12/1991 | Sinofsky | |
| 5,078,150 A | 1/1992 | Hara et al. | |
| 5,090,400 A | 2/1992 | Saito | |
| 5,091,652 A | 2/1992 | Mathies et al. | |
| 5,115,137 A | 5/1992 | Andersson-Engels et al. | |
| 5,117,466 A | 5/1992 | Buican et al. | |
| 5,125,404 A | 6/1992 | Kittrell et al. | |
| 5,131,398 A | 7/1992 | Alfano et al. | |
| 5,134,662 A | 7/1992 | Bacus et al. | |
| 5,165,079 A | 11/1992 | Schulz-Hennig | |
| 5,178,616 A | 1/1993 | Uemiya et al. | |
| 5,196,928 A | 3/1993 | Karasawa et al. | |
| 5,214,503 A | 5/1993 | Chiu et al. | |
| 5,225,883 A | 7/1993 | Carter et al. | |
| 5,255,087 A | 10/1993 | Nakamura et al. | |
| 5,279,298 A | 1/1994 | Flower | |

(Continued)

FOREIGN PATENT DOCUMENTS

| | | |
|---|---|---|
| AT | 409451 B | 8/2002 |
| CA | 2212257 A1 | 8/1996 |

(Continued)

OTHER PUBLICATIONS

Akintunde, A. et al. (Oct.-Nov. 1992). "Quadruple Labeling of Brain-Stem Neurons: A Multiple Retrograde Fluorescent Tracer Study of Axonal Collateralization," *Journal of Neuroscience* Methods 45(1-2):15-22.

Alander, J.T. et al. (Jan. 1, 2012). "A Review of Indocyanine Green Fluorescent Imaging in Surgery," *International Journal of Biomedical Imaging* 2012:1-26, article ID 940585.

Alfano et al. (Oct. 1987). "Fluorescence Spectra from Cancerous and Normal Human Breast and Lung Tissues," *IEEE Journal of Quantum Electronics* QE-23(10):1806-1811.

Alm, A. et al. (Jan. 1, 1973). "Ocular and Optic Nerve Blood Flow at Normal and Increased Intraocular Pressures in Monkeys (Macaca irus): A Study with Radioactively Labelled Microspheres Including Flow Determinations in Brain and Some Other Tissues," *Experimental Eye Research* 15(1):15-29.

(Continued)

*Primary Examiner* — D. L. Jones

(74) *Attorney, Agent, or Firm* — Morrison & Foerster LLP

(57) ABSTRACT

The invention provides methods for pre- and intra-operatively localizing penile sentinel lymph nodes by injection of fluorescent dyes into penile tumors.

14 Claims, 2 Drawing Sheets

(56) References Cited

U.S. PATENT DOCUMENTS

| | | |
|---|---|---|
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A | 2/1995 | Flower |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Häfele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,491,343 A | 2/1996 | Brooker |
| 5,496,369 A | 3/1996 | Howard, III |
| 5,507,287 A | 4/1996 | Palcic et al. |
| 5,514,127 A | 5/1996 | Shanks |
| 5,519,534 A | 5/1996 | Smith et al. |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Iijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A | 4/1998 | Hemstreet, III et al. |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,178,340 B1 | 1/2001 | Svetliza |
| 6,179,421 B1 | 1/2001 | Pang |
| 6,186,628 B1 | 2/2001 | Van De Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,217,848 B1 | 4/2001 | Achilefu et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,319,273 B1 | 11/2001 | Cheen et al. |
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Thorn Leeson et al. |
| 6,566,641 B1 | 5/2003 | Suda |
| 6,603,552 B1 | 8/2003 | Cline et al. |
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |
| 6,915,154 B1 | 7/2005 | Docherty et al. |
| 6,936,043 B2 | 8/2005 | Peyman |
| 6,944,493 B2 | 9/2005 | Alam et al. |
| 7,113,817 B1 | 9/2006 | Winchester, Jr. et al. |
| 7,236,815 B2 | 6/2007 | Richards-Kortum et al. |
| 7,364,574 B2 | 4/2008 | Flower |
| 7,381,400 B2 * | 6/2008 | Woltering ............ A61K 49/006 424/1.11 |
| 7,400,753 B2 | 7/2008 | Seino et al. |
| 7,400,755 B2 | 7/2008 | West et al. |
| 7,482,318 B2 | 1/2009 | Aurelian et al. |
| 7,581,191 B2 | 8/2009 | Rice et al. |
| 7,729,750 B2 | 6/2010 | Tromberg et al. |
| 7,774,048 B2 | 8/2010 | Nakaoka et al. |
| 7,881,777 B2 | 2/2011 | Docherty et al. |
| 7,885,438 B2 | 2/2011 | Uppaluri et al. |
| 8,036,437 B2 | 10/2011 | Arditi et al. |
| 8,073,224 B2 | 12/2011 | Strobel et al. |
| 8,144,958 B2 | 3/2012 | Nahm et al. |
| 8,185,176 B2 | 5/2012 | Mangat et al. |
| 8,194,981 B2 | 6/2012 | Suzuki |
| 8,285,353 B2 | 10/2012 | Choi et al. |
| 8,361,775 B2 | 1/2013 | Flower |
| 8,406,860 B2 | 3/2013 | Dvorsky et al. |
| 8,480,579 B2 | 7/2013 | Serov et al. |
| 8,521,260 B2 | 8/2013 | Grinvald et al. |
| 8,538,107 B2 | 9/2013 | Rottger |
| 8,647,605 B2 | 2/2014 | Mangat et al. |
| 8,725,225 B2 * | 5/2014 | Golijanin ............ A61B 5/0071 600/317 |
| 8,892,190 B2 | 11/2014 | Docherty et al. |
| 8,929,974 B2 | 1/2015 | Hauger et al. |
| 8,965,488 B2 | 2/2015 | Dvorsky et al. |
| 9,089,601 B2 * | 7/2015 | Golijanin ........... A61K 49/0034 |
| 9,129,366 B2 | 9/2015 | Nahm et al. |
| 9,241,636 B2 | 1/2016 | Koizumi et al. |
| RE45,916 E * | 3/2016 | Golijanin ............ A61B 5/0071 |
| 9,351,644 B2 | 5/2016 | Nahm et al. |
| 9,357,931 B2 | 6/2016 | Nahm et al. |
| 9,421,280 B2 | 8/2016 | Mangat et al. |
| 9,610,021 B2 | 4/2017 | Dvorsky et al. |
| 9,642,532 B2 | 5/2017 | Fengler et al. |
| 9,816,930 B2 * | 11/2017 | Moriyama ......... A61B 1/00009 |

(56) References Cited

U.S. PATENT DOCUMENTS

| | | |
|---|---|---|
| 9,936,887 B2 | 4/2018 | Dvorsky et al. |
| 10,041,042 B2 | 8/2018 | Flower |
| 10,219,742 B2 | 3/2019 | Dvorsky et al. |
| 10,265,419 B2 | 4/2019 | Golijanin |
| 2002/0025541 A1 | 2/2002 | Nelson et al. |
| 2002/0038120 A1 | 3/2002 | Duhaylongsod et al. |
| 2002/0099279 A1 | 7/2002 | Pfeiffer et al. |
| 2002/0099295 A1 | 7/2002 | Gil et al. |
| 2002/0146369 A1 | 10/2002 | Goldenberg |
| 2002/0181752 A1 | 12/2002 | Wallo et al. |
| 2002/0183621 A1 | 12/2002 | Pfeiffer et al. |
| 2003/0032885 A1 | 2/2003 | Rubinstein et al. |
| 2003/0050543 A1 | 3/2003 | Hartmann |
| 2003/0060718 A1 | 3/2003 | Alam et al. |
| 2003/0060722 A1 | 3/2003 | Pfeiffer et al. |
| 2003/0064025 A1 | 4/2003 | Yang et al. |
| 2003/0093064 A1 | 5/2003 | Peyman |
| 2003/0093065 A1 | 5/2003 | Peyman |
| 2003/0156252 A1 | 8/2003 | Morris et al. |
| 2003/0187349 A1 | 10/2003 | Kaneko et al. |
| 2003/0232016 A1 | 12/2003 | Heinrich |
| 2003/0236458 A1 | 12/2003 | Hochman |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1 | 9/2004 | Levine |
| 2005/0019744 A1 | 1/2005 | Bertuglia |
| 2005/0020891 A1 | 1/2005 | Rubinstein et al. |
| 2005/0033145 A1 | 2/2005 | Graham et al. |
| 2005/0069525 A1 | 3/2005 | Mikael |
| 2005/0089866 A1 | 4/2005 | Hinuma et al. |
| 2005/0107380 A1 | 5/2005 | Nimmo et al. |
| 2005/0142556 A1* | 6/2005 | Hoon ................ A61K 49/006 435/6.14 |
| 2005/0182321 A1 | 8/2005 | Frangioni |
| 2005/0182327 A1 | 8/2005 | Petty et al. |
| 2005/0182431 A1 | 8/2005 | Hausen et al. |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0254008 A1 | 11/2005 | Ferguson et al. |
| 2006/0013768 A1 | 1/2006 | Woltering |
| 2006/0079750 A1 | 4/2006 | Fauci et al. |
| 2006/0108509 A1 | 5/2006 | Frangioni et al. |
| 2006/0118742 A1 | 6/2006 | Levenson et al. |
| 2006/0147897 A1 | 7/2006 | Grinvald et al. |
| 2006/0239921 A1 | 10/2006 | Mangat et al. |
| 2006/0241499 A1 | 10/2006 | Irion et al. |
| 2007/0121099 A1 | 5/2007 | Matsumoto et al. |
| 2007/0122344 A1 | 5/2007 | Golijanin |
| 2007/0122345 A1 | 5/2007 | Golijanin |
| 2007/0203413 A1 | 8/2007 | Frangioni |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0025918 A1 | 1/2008 | Frangioni et al. |
| 2008/0044073 A1 | 2/2008 | Bernhardt et al. |
| 2008/0081990 A1 | 4/2008 | Berenfeld et al. |
| 2008/0161744 A1 | 7/2008 | Golijanin et al. |
| 2008/0221421 A1 | 9/2008 | Choi et al. |
| 2008/0221648 A1 | 9/2008 | Flower |
| 2008/0239070 A1 | 10/2008 | Westwick et al. |
| 2008/0319309 A1 | 12/2008 | Bredno et al. |
| 2009/0005693 A1 | 1/2009 | Brauner et al. |
| 2009/0042179 A1 | 2/2009 | Peltie et al. |
| 2009/0048516 A1 | 2/2009 | Yoshikawa et al. |
| 2009/0054788 A1 | 2/2009 | Hauger et al. |
| 2009/0118623 A1 | 5/2009 | Serov et al. |
| 2009/0137902 A1 | 5/2009 | Frangioni et al. |
| 2009/0252682 A1 | 10/2009 | Hillman |
| 2009/0297004 A1 | 12/2009 | Baumgart |
| 2010/0016669 A1 | 1/2010 | Takaoka et al. |
| 2010/0022898 A1 | 1/2010 | Rubinstein et al. |
| 2010/0036217 A1 | 2/2010 | Choi et al. |
| 2010/0061604 A1 | 3/2010 | Nahm et al. |
| 2010/0069759 A1 | 3/2010 | Schuhrke et al. |
| 2010/0099961 A1 | 4/2010 | Hubner et al. |
| 2010/0222673 A1 | 9/2010 | Mangat et al. |
| 2010/0286529 A1 | 11/2010 | Carroll et al. |
| 2011/0001061 A1 | 1/2011 | Ishihara |
| 2011/0013002 A1 | 1/2011 | Thompson et al. |
| 2011/0063427 A1 | 3/2011 | Fengler et al. |
| 2011/0071403 A1 | 3/2011 | Sevick-Muraca et al. |
| 2011/0098685 A1 | 4/2011 | Flower |
| 2011/0306877 A1 | 12/2011 | Dvorsky et al. |
| 2012/0026325 A1 | 2/2012 | Bunker et al. |
| 2012/0078093 A1 | 3/2012 | Flower |
| 2012/0165627 A1 | 6/2012 | Yamamoto |
| 2012/0165662 A1 | 6/2012 | Nahm et al. |
| 2012/0271176 A1 | 10/2012 | Moghaddam et al. |
| 2013/0203082 A1 | 8/2013 | Gonda et al. |
| 2013/0230866 A1 | 9/2013 | Miyashita et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0342674 A1 | 12/2013 | Dixon |
| 2013/0345560 A1 | 12/2013 | Ferguson, Jr. et al. |
| 2014/0099007 A1 | 4/2014 | Sarkar et al. |
| 2014/0308656 A1 | 10/2014 | Flower |
| 2014/0316262 A1 | 10/2014 | Havens |
| 2015/0112192 A1 | 4/2015 | Docherty et al. |
| 2015/0112193 A1 | 4/2015 | Docherty et al. |
| 2015/0196208 A1 | 7/2015 | Dvorsky et al. |
| 2015/0230710 A1 | 8/2015 | Nahm et al. |
| 2015/0230715 A1 | 8/2015 | Nahm et al. |
| 2016/0038027 A1 | 2/2016 | Brzozowski et al. |
| 2016/0041098 A1 | 2/2016 | Hirawake et al. |
| 2016/0199515 A1 | 7/2016 | Flower |
| 2016/0371834 A1 | 12/2016 | Watanabe et al. |
| 2017/0039710 A1 | 2/2017 | Minai et al. |
| 2017/0303800 A1 | 10/2017 | Flower et al. |
| 2018/0020933 A1 | 1/2018 | Dvorsky et al. |
| 2018/0120230 A1 | 5/2018 | Moriyama et al. |
| 2018/0220907 A1 | 8/2018 | Dvorsky et al. |
| 2018/0234603 A1 | 8/2018 | Moore et al. |

FOREIGN PATENT DOCUMENTS

| | | |
|---|---|---|
| CA | 2413033 A1 | 3/2000 |
| CA | 2711560 A1 | 7/2009 |
| CN | 1049781 A | 3/1991 |
| CN | 1200174 A | 11/1998 |
| CN | 1399528 A | 2/2003 |
| CN | 101264014 A | 9/2008 |
| DE | 3906860 A1 | 9/1989 |
| DE | 19608027 A1 | 9/1996 |
| DE | 10028233 A1 | 1/2002 |
| DE | 10120980 A1 | 11/2002 |
| DE | 69727220 T2 | 12/2004 |
| DE | 102005044531 A1 | 3/2007 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0807402 A1 | 11/1997 |
| EP | 0826335 A1 | 3/1998 |
| EP | 1677097 A1 | 7/2006 |
| EP | 1761171 A | 3/2007 |
| EP | 1874181 A | 1/2008 |
| GB | 2203831 A | 10/1988 |
| JP | S58-222331 A | 12/1983 |
| JP | S59-069721 A | 4/1984 |
| JP | S59-070903 A | 4/1984 |
| JP | H01-236879 A | 9/1989 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | H07-043303 A | 2/1995 |

(56) References Cited

FOREIGN PATENT DOCUMENTS

| | | |
|---|---|---|
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | H09-308609 A | 12/1997 |
| JP | H09-309845 A | 12/1997 |
| JP | H10-500479 A | 1/1998 |
| JP | H10-503480 B1 | 3/1998 |
| JP | H10-085222 A | 4/1998 |
| JP | H10-104070 A | 4/1998 |
| JP | H10-151104 A | 6/1998 |
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2001-198079 A | 7/2001 |
| JP | 2002-219129 A | 8/2002 |
| JP | 2003-510121 A | 3/2003 |
| JP | 2003-144401 A | 5/2003 |
| JP | 2003-329589 A | 11/2003 |
| JP | 2004-528917 A | 9/2004 |
| JP | 2004-325200 A | 11/2004 |
| JP | 2006-503620 A | 2/2006 |
| JP | 2006-192280 A | 7/2006 |
| JP | 2007-021006 A | 2/2007 |
| JP | 3896176 B2 | 3/2007 |
| JP | 2008-525126 A | 7/2008 |
| JP | 2008-535600 A | 9/2008 |
| JP | 2008-231113 A | 10/2008 |
| JP | 2009-095683 A | 5/2009 |
| JP | 2009-291554 A | 12/2009 |
| JP | 2010-505582 A | 2/2010 |
| JP | 2011-509768 A | 3/2011 |
| JP | 2011-519589 A | 7/2011 |
| JP | 2011-528918 A | 12/2011 |
| JP | 5918532 B2 | 5/2016 |
| KR | 1990-0005434 B1 | 7/1990 |
| KR | 2002-0064287 A | 8/2002 |
| RU | 2288633 C1 | 12/2006 |
| WO | WO-1986/02730 A1 | 5/1986 |
| WO | WO-1990/10219 A1 | 9/1990 |
| WO | WO-1990/12536 A1 | 11/1990 |
| WO | WO-1993/25141 A1 | 12/1993 |
| WO | WO-1994/12092 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | WO-2001/08552 A1 | 2/2001 |
| WO | WO-2001/17561 A1 | 3/2001 |
| WO | WO-2001/22870 A1 | 4/2001 |
| WO | WO-2001/39764 A2 | 6/2001 |
| WO | WO-2001/69244 A2 | 9/2001 |
| WO | WO-2001/80734 A1 | 11/2001 |
| WO | WO-2001/82786 A2 | 11/2001 |
| WO | WO-2002/061390 A2 | 8/2002 |
| WO | WO-2003/006658 A1 | 1/2003 |
| WO | WO-2004/006963 A1 | 1/2004 |
| WO | WO-2004/052195 A1 | 6/2004 |
| WO | WO-2005/026319 A2 | 3/2005 |
| WO | WO-2005/034747 A1 | 4/2005 |
| WO | WO-2005/036143 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/028032 A2 | 3/2007 |
| WO | WO-2008/039968 A2 | 4/2008 |
| WO | WO-2008/044822 A1 | 4/2008 |
| WO | WO-2008/070269 A2 | 6/2008 |
| WO | WO-2008/070269 A3 | 6/2008 |
| WO | WO-2008/087869 A1 | 7/2008 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2012/038824 A1 | 3/2012 |
| WO | WO-2012/096878 A2 | 7/2012 |
| WO | WO-2013/190391 A2 | 12/2013 |
| WO | WO-2015/001427 A2 | 1/2015 |
| WO | WO-2013/002350 A1 | 2/2015 |

OTHER PUBLICATIONS

Alonso-Burgos, A. et al. (2006). "Preoperative planning of deep inferior epigastric artery perforator flap reconstruction with multi-slice-CT angiography: imaging findings and initial experience," *Journal of Plastic, Reconstructive & Aesthetic Surgery* 59:585-593.

Alvarez, F. J. et al. (Apr. 1996). "Behaviour of Isolated Rat and Human Red Blood Cells Upon Hypotonic-Dialysis Encapsulation Of Carbonic Anhydrase and Dextran," *Biotechnology and Applied Biochemistry* 23(2):173-179.

Ancalmo, N. et al. (1997). "Minimally invasive coronary artery bypass surgery: really minimal?" *Ann. Thorac. Surg.* 64:928-929.

Andersson-Engels, S. et al. (1991). "Fluorescence Characteristics of Atherosclorotic Plaque and Malignant Tumors," in *Optical Methods for Tumor Treatment and Early Diagnosis: Mechanisms and Techniques*, T. J. Dougherty (Ed.), the Society of Photo-optical Instrumentation Engineers (SPIE) 1426:31-43, fourteen pages.

Andersson-Engels, S. et al. (Mar. 1989). "Tissue Diagnostics Using Laser-Induced Fluorescence," *Berichte der Bunsengesellschaft für physikalische Chemie* 93(3):335-342.

Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.

Annese, V. et al. (2005). "Erthrocytes-Mediated Delivery of Dexamethasone in Steroid-Dependent IBD Patients—a Pilot Uncontrolled Study," *American Journal of Gastroenterology* 100:1370-1375.

Argus-50/CA, Inter cellular CA2+ (calcium ion) Image Analysis system (Feb. 1992). "Observation and 2-dimensional analysis of Ca2+ concentration distribution. Fura-2 and Indo-1 compatible. Ca2+ concentrations are calculated from the fluorescence ratio," pp. 1-10.

Author Unknown. (Jun. 4, 2008)."Invitrogen," Material Safety Data Sheet, p. 1-4.

(56) References Cited

OTHER PUBLICATIONS

Awano, T. et al. (Jun. 2010). "Intraoperative EC-IC Bypass Blood Flow Assessment with Indocyanine Green Angiography in Moyamoya and Non-Moyamoya Ischemic Stroke," *World Neurosurg.* 73(6):668-674.

Azuma, R. et al. (2008, presented in part Jun. 2007). "Detection of Skin Perforators by Indocyanine Green Fluorescence Nearly Infrared Angiography," *PRS Journal* 122(4):1062-1067.

Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.

Barton, J.K. et al. (1999) "Simultaneous irradiation and imaging of blood vessels during pulsed laser delivery," *Lasers in Surgery and Medicine* 24(3):236-243.

Bassingthwaighte, J.B. et al. (Apr. 1974). "Organ Blood Flow, Wash-in, Washout, and Clearance of Nutrients and Metabolites," *Mayo Clin. Proc.* 49(4):248-255.

Batliwala, H. et al. (Apr. 15, 1995). "Methane-Induced Haemolysis of Human Erythrocytes," *Biochemical J.* 307(2):433-438.

Bek, T. (1999). "Diabetic Maculopathy Caused by Disturbances in Retinal Vasomotion: A New Hypothesis," *Acta Ophthalmologica Scandinavica* 77:376-380.

Benson, R.C. et al. (1978). "Fluorescence Properties of Indocyanine Green as Related to Angiography," *Phys. Med. Biol.* 23(1):159-163.

Black's Medical Dictionary, "Perfusion," 42nd Edition (2009), two pages.

Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.

Boldt, .J. et al. (Feb. 1990). "Lung management during cardiopulmonary bypass: influence on extravascular lung water," *Journal of Cardiothoracic Anesthesia* 4(1):73-79.

Boldt, J. et al. (1991). "Does the technique of cardiopulmonary bypass affect lung water content?" *European Journal of Cardio-Thoracic Surgery* 5:22-26.

Bütter, A. et al. (May 2005). "Melanoma in Children and the Use of Sentinel Lymph Node Biopsy," *Journal of Pediatric Surgery* 40(5):797-800.

C2741, Compact High Performance video camera for industrial applications with Built-in contrast enhancement circuit, Jun. 1998, six pgs.

Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.

Coffey, J.H. et al. (1984). "Evaluation of Visual Acuity During Laser Photoradiation Therapy of Cancer," *Lasers in Surgery and Medicine* 4(1):65-71.

Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.

Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.

Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.

Dail, W.G. et al. (Oct. 1999). "Multiple Vasodilator Pathways from the Pelvic Plexus to the Penis of the Rat," *International Journal of Impotence Research* 11(5):277-285.

Dan, A.G. et al. (Nov. 2004). "1% Lymphazurin vs 10% Fluorescein for Sentinel Node Mapping in Colorectal Tumors," *Arch Surg.* 139(11):1180-1184.

Daniels, G. et al. (Apr. 2007). "Towards Universal Red Blood Cell," *Nature Biotechnology* 25(4):427-428.

De Flora, A. (Sep. 1986). "Encapsulation of Adriamycin in human erythrocytes," *Proc. Natl. Acad. Sci., USA* 83(18):7029-7033.

Declaration of Brian Wilson dated Aug. 22, 2017 for Inter Partes Review No. IPR2017-01426, twelve pages.

Definition of "Expose," Excerpt of Merriam Webster's Medical Desk Dictionary (1993), four pages.

Definition of "Graft," Excerpt of Stedman's Medical Dictionary for the Health Professions and Nursing; 6th Ed. (2008), three pages.

De-Grand, A.M. et al. (Dec. 2003). "An Operational Near Infrared Fluorescence Imaging System Prototype for Large Animal Surgery," *Technology in Cancer Research & Treatment* 2(6):1-10.

Deloach, J.R. (ed.) et al. (1985). *Red Blood Cells as Carriers for Drugs. A Method for Disseminating Chemotherapeutics, Hormones, Enzymes and Other Therapeutic Agents via the Circulatory System,* Karger, Basel, CH, pp. v-vii, (Table of Contents), seven pages.

Deloach, J. R. (Jun. 1983). "Encapsulation of Exogenous Agents in Erythrocytes and the Circulating Survival of Carrier Erythrocytes," *Journal of Applied Biochemistry* 5(3):149-157.

Demos (May/Jun. 2004). "Near-Infrared Autofluorescence Imaging for Detection of Cancer," *Journal of Biomedical Optics* 9(3):587-592.

Desai, N.D. et al. (Oct. 18, 2005, e-published on Sep. 28, 2005) "Improving the Quality of Coronary Bypass Surgery with Intraoperative Angiography," *Journal of the American College of Cardiology* 46(8):1521-1525.

Detter, C. et al. (Aug. 28, 2007). "Fluorescent Cardiac Imaging: A Novel Intraoperative Method for Quantitative Assessment of Myocardial Perfusion During Graded Coronary Artery Stenosis," *Circulation* 116(9):1007-1014.

Detter, C. et al. (Jun. 2002). "Near-Infrared Fluorescence Coronary Angiography: A New Noninvasive Technology for Intraoperative Graft Patency Control." *The Heart Surgery Forum #2001-6973* 5(4):364-369.

Dietz, F.B. et al. (Feb. 2003). "Indocyanine Green: Evidence of Neurotoxicity in Spinal Root Axons," *Anesthesiology* 98(2):516-520.

Digital CCD Microscopy (date unknown). Chapter 14, pp. 259-282.

Dougherty, T.J. et al. (1990). "Cutaneous Phototoxic Occurrences in Patients Receiving Photofrin," *Lasers in Surgery and Medicine* 10(5):485-488.

Draijer, M.J. et al. (Jun. 17-19, 2007). "Laser Doppler Perfusion Imaging with a High-Speed CMOS-Camera," in *Novel Optical Instrumentation for Biomedical Applications III,* C. Depeursinge, ed., Proceedings of SPIE-OSA Biomedical Optics (Optical Society of America, 2007), SPIE-OSA, 6631:0N1-0N7, eight pages.

Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.

Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.

Emery R.W. et al. (Aug. 1996). "Revascularization Using Angioplasty and Minimally Invasive Techniques Documented by Thermal Imaging," *The Annals of Thoracic Surgery* 62(2):591-593.

Enquist, L.W. et al. (2002). "Directional Spread of an α-Herpesvirus in the Nervous System," *Veterinary Microbiology* 86:5-16.

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

Falk, T. et al. (Apr. 15, 2001). "A Herpes Simplex Viral Vector Expressing Green Fluorescent Protein can be Used to Visualize Morphological Changes in High-density Neuronal Culture," *Electronic Journal of Biotechnology* 4(1):34-45.

Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9(2):103-114.

Flower, R.W. (1992). "Choroidal Angiography Today and Tomorrow," *Retina* 12(3):189-190.

Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.

Flower, R.W. (Aug. 2002). "Optimizing Treatment of Choroidal Neovascularization Feeder Vessels Associated with Age-Related Macular Degeneration," *American Journal of Ophthalmology* 134(2):228-239.

(56) References Cited

OTHER PUBLICATIONS

Flower, R.W. (Dec. 1973). "Injection Technique for Indocyanine Green and Sodium Fluorescein Dye Angiography of the Eye," *Investigative Opthamology* 12(12):881-895.
Flower, R.W. (Sep. 1, 1994). "Does Preinjection Binding of Indocyanine Green to Serum Actually Improve Angiograms?," *Arch Ophthalmol.* 112(9):1137-1139.
Flower, R.W. et al. (Aug. 1977). "Quantification of Indicator Dye Concentration in Ocular Blood Vessels," *Exp. Eye Res.* 25(2):103-111.
Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," *Investigative Ophthalmology, & Visual Science* 49(12):5510-5516.
Flower, R.W. et al. (Mar. 26, 2008- Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).
Forrester et al. (Nov. 1, 2002). "Comparison of Laser Speckle and Laser Doppler Perfusion Imaging: Measurement in Human Skin and Rabbit Articular Tissue," *Medical and Biological Engineering and Computing* 40(6):687-697.
Frangioni, J.V. (Oct. 2003). "*In Vivo* Near-Infrared Fluorescence Imaging," *Current Opinion in Chemical Biology* 7(5):626-634.
Frenzel H. et al. (Apr. 18, 2008). "In Vivo Perfusion Analysis of Normal and Dysplastic Ears and its Implication on Total Auricular Reconstruction," *Journal of Plastic, Reconstructive and Aesthetic Surgery* 61(Supplement1):S21-S28.
Fritzsch, B. et al. (Aug. 1991)."Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.
Gagnon, A.R. et al. (2006). "Deep and Superficial Inferior Epigastric Artery Perforator Flaps," *Cirugia Plástica Ibero-Latinoamericana* 32(4):7-13.
Gardner, T.J. (1993). "Coronary Artery Disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.
Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.
Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal of Physical Chemistry A* 107(18):3443-3449.
Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.
Giunta, R.E. et al. (Jul. 2005). "Prediction of Flap Necrosis with Laser Induced Indocyanine Green Fluorescence in a Rat Model," *British Journal of Plastic Surgery* 58(5):695-701.
Giunta, R.E. et al. (Jun. 2000). "The Value of Preoperative Doppler Sonography for Planning Free Perforator Flaps," *Plastic and Reconstructive Surgery* 105(7):2381-2386.
Glossary, Nature, downloaded from the internet <http://www.nature.com/nrg/journal/v4/nl0/glossary/nrgl 183_glossary.html>> HTML on Jun. 30, 2014, three pages.
Glover, J.C. et al. (Nov. 1986). "Fluorescent Dextran-Amines Used as Axonal Tracers in the Nervous System of the Chicken Embryo," *Journal of Neuroscience Methods* 18(3):243-254.
Goldstein, J.A. et al. (Dec. 1998). "Intraoperative Angiography to Assess Graft Patency After Minimally Invasive Coronary Bypass," *Ann. Thorac. Surg.* 66(6):1978-1982.
Gothoskar A.V. (Mar. 2004). "Resealed Erythrocytes: A Review," *Pharmaceutical Technology* pp. 140, 142, 144, 146, 148, 150, 152 and 154-158, twelve pages.

Granzow, J.W. et al. (Jul. 2007)."Breast Reconstruction with Perforator Flaps" *Plastic and Reconstructive Surgery* 120(1):1-12.
Green, H.A. et al. (Jan. 1992). "Burn Depth Estimation Using Indocyanine Green Fluorescence," *Arch Dermatol* 128(1):43-49.
Haglund, M. et al. (Feb. 1996). "Enhanced Optical Imaging of Human Gliomas and Tumor Margins," *Neurosurgery* 38(2):308-317.
Haglund, M.M. et al. (Nov. 1994). "Enhanced Optical Imaging of Rat Gliomas and Tumor Margins," *Neurosurgery* 35(5):930-941.
Hallock, G.G. (Jul. 2003). "Doppler Sonography and Color Duplex Imaging for Planning a Perforator Flap," *Clinics in Plastic Surgery* 30(3):347-357.
Hamamatsu Brochure. (May 1997). Specifications for Real-time Microscope Image Processing System: ARGUS-20 with C2400-75i, four pages.
Hamamatsu. (Date unknown). Microscope Video Camera, for Fluorescent Observation, Easy Fluorescent Image Analysis C2400-731, -751 Series a CCD Camera, seven pages.
Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.
Hayata, Y. et al. (Jul. 1982). "Fiberoptic Bronchoscopic Laser Photoradiation for Tumor Localization in Lung Cancer," *Chest* 82(1)10-14.
He, Z. (Feb. 2009). "Fluorogold Induces Persistent Neurological Deficits and Circling Behavior in Mice Over-Expressing Human Mutant Tau," *Current Neurovascular Research* 6(1):54-61.
Herts, B.R. (May 2003). "Imaging for Renal Tumors," *Current Opin. Urol.* 13(3):181-186.
Hirano, T. et al. (1989). "Photodynamic Cancer Diagnosis and Treatment System Consisting of Pulse Lasers and an Endoscopic Spectro-Image Analyzer," *Laser in Life Sciences* 3(2):99116.
Holm, C. et al. (2002). "Monitoring Free Flaps Using Laser-Induced Fluorescence of Indocyanine Green: A Preliminary Experience," *Microsurgery* 22(7):278-287.
Holm, C. et al. (Apr. 2003, e-published on Feb. 25, 2003). "Laser-Induced Fluorescence of Indocyanine Green: Plastic Surgical Applications," *European Journal of Plastic Surgery* 26(1):19-25.
Holm, C. et al. (Dec. 1, 2002). "Intraoperative Evaluation of Skin-Flap Viability Using Laser-Induced Fluorescence of Indocyanine Green," *British Journal of Plastic Surgery* 55(8):635-644.
Humblet, V. et al. (Oct. 2005). "High-Affinity Near-Infrared Fluorescent Small-Molecule Contrast Agents for in Vivo Imaging of Prostate-Specific Membrane Antigen," *Molecular Imaging* 4(4):448-462.
Hung, J. et al.(1991). "Autofluorescence of Normal and Malignant Bronchial Tissue," *Lasers in Surgery and Medicine* 11(2):99-105.
Hyvärinen, L. et al. (1980). "Indocyanine Green Fluorescence Angiography." *Acta ophthalmologica* 58(4):528-538.
Ikeda, S. (Jul. 1989). "Bronichial Telivision Endoscopy," *Chest* 96(1):41S-42S.
Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.
Jagoe, J.R. et al. (1989). "Quantification of retinal damage during cardiopulmonary bypass," Third International Conference on Image Processing and its Applications (Conf. Publ. No. 307), IEE, pp. 319-323.
Jamis-Dow, C.A. et al. (Mar. 1996). "Small (< or = 3-cm) Renal Masses: Detection with CT versus US and Pathologic Correlation," *Radiology* 198(3):785-788.
Jolion, J. et al. (Aug. 1991). "Robust Clustering with Applications in Computer Vision," *IEEE Transactions on Pattern Analysis and Machine Intelligence* 13(8):791-802.
Kamolz, L.-P. et al. (Dec. 2003). "Indocyanine Green Video Angiographies Help to Identify Burns Requiring Operation," *Burns* 29(8):785-791.
Kapadia, C. R. et al. (Jul. 1990). "Laser-Induced Fluorescence Spectroscopy of Human Colonic Mucosa. Detection of Adenomatous Transformation," *Gastroenterology* 99(1):150-157.

(56) References Cited

OTHER PUBLICATIONS

Kato, H. et al. (Jun. 1985). "Early Detection of Lung Cancer by Means of Hematoporphyrin Derivative Fluorescence and Laser Photoradiation," *Clinics in Chest Medicine* 6(2):237-253.

Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.

Keon, W.J. et al. (Dec. 1979). "Coronary Endarterectomy: An Adjunct to Coronary Artery Bypass Grafting," *Surgery* 86(6):859-867.

Kim, S. et al. (Jan. 2004, e-published Dec. 7, 2003). "Near-Infrared Fluorescent Type II Quantum Dots for Sentinel Lymph Node Mapping," *Nature Biotechnology* 22(1):93-97.

Kiryu, J. et al. (Sep. 1994). "Noninvasive Visualization of the Choriocapillaris and its Dynamic Filling," *Investigative Ophthalmology & Visual Science* 35(10):3724-3731.

Kitai, T. et al. (Jul. 2005). "Fluorescence Navigation with Indocyanine Green for Detecting Sentinel Lymph Nodes in Breast Cancer," *Breast Cancer* 12(3):211-215.

Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.

Köbbert, C. et al. (Nov. 2000). "Current Concepts in Neuroanatomical Tracing," *Progress in Neurobiology* 62(4):327-351.

Kokaji, K. et al. (Date Unknown). "Intraoperative Quality Assessment by Using Fluorescent Imaging in Off-pump Coronary Artery Bypass Grafting," *The Department of Cardiovascular Surgery, University of Keio*, Tokyo, Japan, one page. (Abstract only).

Kömürcü, F. et al. (Feb. 2005). "Management Strategies for Peripheral Iatrogenic Nerve Lesions," *Annals of Plastic Surgery* 54(2):135-139.

Krishnan, K. G. et al. (Apr. 1, 2005). "The Role of Near-Infrared Angiography in the Assessment of Post-Operative Venous Congestion in Random Pattern, Pedicled Island and Free Flaps", *British Journal of Plastic Surgery* 58(3):330-338.

Kuipers, J.A. et al. (1999). "Recirculatory and Compartmental Pharmacokinetic Modeling of Alfentanil Pigs, the Influence of Cardiac Output," *Anesthesiology* 90(4):1146-1157.

Kupriyanov, V.V. et al. (Nov. 2004, e-publication Sep. 28, 2004). "Mapping Regional Oxygenation and Flow in Pig Hearts In Vivo Using Near-infrared Spectroscopic Imaging," *Journal of Molecular and Cellular Cardiology* 37(5):947-957.

Kurihara, K. et al. (Jun. 1984). "Nerve Staining with Leucomethylene Blue: An Experimental Study," *Plastic and Reconstruction Surgery* 73(6):960-964.

Kyo, S. (Date Unknown). "Use of Ultrasound Cardiology during Coronary Artery Bypass Surgery," *Heart and Blood Vessel Imaging II*, three pages.

Lam, S. et al. (1991). "Mechanism of Detection of Early Lung Cancer by Ratio Fluorometry," *Lasers in Life Sciences* 4(2):67-73.

Lam, S. et al. (Feb. 1990). "Detection of Early Lung Cancer Using Low Dose Photofrin II," *Chest* 97(2):333-337.

Lam, S. et al. (Jul. 1, 1990). "Detection of Lung Cancer by Ratio Fluorometry With and Without Photofrin II," *Proc. SPIE—Optical Fibers in Medicine V* 1201:561-568.

Lam, S. et al. (Nov. 1-4, 1990). "Fluorescence Imaging of Early Lung Cancer," *Annual International Conference of the IEEE Engineering in Medicine and Biology Society* 12(3):1142-1143.

Lam, S.C. et al. (1993). "Fluorescence Detection," Chapter 20 in *Lung Cancer*, Roth, J.A. (ed.), et al., Blackwell Scientific Publications Inc., 238 Main Street, Cambridge, Massachusetts, 02142, pp. 325-338, sixteen pages.

Lanciego, J.L. et al. (Jun. 1998). "Multiple Neuroanatomical Tracing in Primates," *Brain Research Protocols* 2(4):323-332.

Lanciego, J.L. et al. (Oct. 1998). "Multiple Axonal Tracing: Simultaneous Detection of Three Tracers in the Same Section," *Histochemistry and Cell Biology* 110(5):509-515.

Laub G.W. et al. (Nov./Dec. 1989). "Experimental Use of Fluorescein for Visualization of Coronary Arteries," *Vascular and Endovascular Surgery* 23(6):454-457.

Lee, E.T. et al. (Mar. 1997). "A New Method for Assessment of Changes in Retinal Blood Flow," *Medical Engineering & Physics* 19(2):125-130.

Leissner, J. et al. (Jan. 2004). "Extended Radical Lymphadenectomy in Patients with Urothelial Bladder Cancer: Results of a Prospective Multicenter Study," *The Journal of Urology* 171(1):139-144.

Leithner, C. (Jul. 14, 2003). "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/d issertationen/leith nerch ristoph-2003-07-14/>, two hundred and eight pages [English Abstract and Machine Translation].

Liedberg, F. et al. (2003). "Sentinel-Node-Diagnostik Beim Invasiven (Bladder Cancer and the Sentinel Node Concept)," *Aktuel Urol.* 34:115-118, (English Abstract Only).

Liedberg, F. et al. (Jan. 2006). "Intraoperative Sentinel Node Detection Improves Nodal Staging in Invasive Bladder Cancer," *The Journal of Urology* 175(1):84-89.

Lippincott's New Medical Dictionary. "Perfusion," p. 707 (1897), three pages.

Liptay, M.J. (Mar. 2004). "Sentinel Node Mapping in Lung Cancer," *Annals of Surgical Oncology* 11(Supplement 3):271S-274S.

Little, J.R. et al. (May 1979). "Superficial Temporal Artery to Middle Cerebral Artery Anastomosis: Intraoperative Evaluation by Fluorescein Angiography and Xenon—133 Clearance," *Journal of Neurosurgery* 50(5):560-569.

Liu Q. P. et al. (Apr. 2007). "Bacterial Glycosidases for the Production of Universal Red Blood Cells" *Nature Biotechnology* 25(7):454-464.

Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.

Mack, M.J. et al. (Sep. 1998). "Arterial Graft Patency in Coronary Artery Bypass Grafting: What Do We Really Know?," *Ann. Thorac. Surg.* 66(3):1055-1059.

Magnani, M. et al. (1998). "Erythrocyte Engineering for Drug Delivery and Targeting," *Biotechnol. Appl. Biochem.* 28:1-6.

Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.

Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.

Malmström, P.U. et al. (Jul. 2004). "RE: Extended Radical Lymphadenectomy in Patients With Urothelial Bladder Cancer: Results of a Prospective Multicenter Study," *J. of Urol.* 172(1):386, one page.

Marangos, N. et al. (Dec. 2001). "In Vivo Visualization of the Cochlear Nerve and Nuclei with Fluorescent Axonal Tracers," *Hearing Research* 162(1-2):48-52.

Martinez-Pérez, M. et al. (Sep. 19, 1996). "Unsupervised Segmentation Based on Robust Estimation and Cooccurrence Data," *Proceedings of the International Conference on Miage Processing (ICIP) Lausanne* 3:943-945.

May, S. (May/Jun. 1995). "Photonic Approaches to Burn Diagnostics," *Biophotonics International* pp. 44-50.

Mckee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.

Merriam Webster Medline Plus Medical Dictionary. "Perfusion," located at http://www.merriam-webster.com/medlineplus/perfusion, last visited on Apr. 15, 2015, one page.

Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" *Journal of Neuroscience Methods* 38(2-3):183-191.

(56) References Cited

OTHER PUBLICATIONS

Mitaka USA, Inc. (2015). "PDE Breast Free Flap Evaluation," located at <http://mitakausa.com/category/pde_education/flaps/>, last visited on Oct. 7, 2016, four pages.
Mitaka USA, Inc. (2015). "PDE-Neo" located at <http://mitakausa.com/pde-neo/>, last visited on Oct. 7, 2016, two pages.
Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.
Montän, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.
Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-1024.
Motomura, K. et al. (1999). "Sentinel Node Biopsy Guided by Indocyanine Green Dye in Breast Cancer Patients," *Japan J. Clin. Oncol.* 29(12):604-607.
Mullooly, V.M. et al. (1990). "Dihematoporphyrin Ether-Induced Photosensitivity in Laryngeal Papilloma Patients," *Lasers in Surgery and Medicine* 10(4):349-356.
Murphy (2001). "Digital CCD Microscopy," Chapter 14 in *Fundamentals of Light Microscopy and Electronic Imaging*, John Wiley and Sons, pp. i-xi and 259-281.
Nahlieli, O. et al. (Mar. 2001). "Intravital Staining with Methylene Blue as an Aid to Facial Nerve Identification in Parotid Gland Surgery" *J. Oral Maxillofac. Surgery* 59(3):355-356.
Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366, seventeen pages.
Nakayama, A. et al. (Oct. 2002). "Functional Near-Infrared Fluorescence Imaging for Cardiac Surgery and Targeted Gene Therapy," *Molecular Imaging* 1(4):365-377.
Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103(1):11-21.
Newman et al. (Oct 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pages.
Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.
Novadaq Technologies Inc. (Jan 29, 2007). "Novadaq Imaging System Receives FDA Clearance for use During Plastic Reconstructive Surgery," *PR Newswire*, three pages.
Novadaq Technologies Inc. (Jan. 19, 2005). 510(k) Summary—Showing X-Ray Fluoroscopy as Predicate Device, Fluorescent Angiographic System, six pages.
Oddi, A. et al. (Jun. 1996). "Intraoperative Biliary Tree Imaging with Cholyl-Lysyl- Fluorescein: An Experimental Study in the Rabbit" *Surgical Laparoscopy & Endoscopy* 6(3):198-200.
Ogata, F. et al. (Jun. 2007). "Novel Lymphography Using Indocyanine Green Dye for Near-Infrared Fluorescence Labeling," *Annals of Plastic Surgery* 58(6):652-655.
Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.
Ooyama, M. (Oct. 12-15, 1994). The 8th Congress of International YAG Laser Symposium, The 15th Annual Meeting of Japan Society for Laser Medicine, Sun Royal Hotel, Japan, eight pages.
Ott, P. (1998). "Hepatic Elimination of Indocyanine Green with Special Reference to Distribution Kinetics and the Influence of Plasma Protein Binding," *Pharmacology & Toxicology* 83(Supp. II):5-48.
Oxford Concise Medical Dictionary. "Perfusion," p. 571 (1980), three pages.
Pagni, S. et al. (Jun. 1997). "Anastomotic Complications in Minimally Invasive Coronary Bypass Grafting," *Ann. Thorac. Surg.* 63(6 Suppl):S64-S67.
Palcic et al. (1991). "Lung Imaging Fluorescence Endoscope: A Device for Detection of Occult Lung Cancer," *Medical Design and Material*, thirteen pages.
Palcic, B. et al. (1990). "Development of a Lung Imaging Fluorescence Endoscope," *Annual International Conference of the IEEE Engineering in Medicine and Biology Society* 12(1):0196-0197.
Palcic, B. et al. (Aug. 1, 1990). "The Importance of Image Quality for Computing Texture Features in Biomedical Specimens," *Proc. SPIE* 1205:155-162.
Palcic, B. et al. (Jun. 1, 1991). "Lung Imaging Fluorescence Endoscope: Development and Experimental Prototype," *Proc. SPIE* 1448:113-117.
Palcic, B. et al. (Mar. 1991). "Detection and Localization of Early Lung Cancer by Imaging Techniques," *Chest* 99(3):742-743.
Pandharlpande, P.V. et al. (Mar. 2005). "Perfusion Imaging of the Liver: Current Challenges and Future Goals," *Radiology* 234(3):661-673.
Paques, M. et al. (Mar. 2003). "Axon-Tracing Properties of Indocyanine Green," *Arch Ophthalmol.* 121(3):367-370.
Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.
Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.
Peak, M.J. et al. (1986). "DNA-to-Protein Crosslinks and Backbone Breaks Caused by FAR-and NEAR-Ultraviolet and Visible Light Radiations in Mammalian Cells," in *Mechanism of DNA Damage and Repair, Implications for Carcinogenesis and Risk Assessment*, Simic, M.G. (ed.) et al., Plenum Press, 233 Spring Street, New York, N.Y. 10013, pp. 193-202.
Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (abstract), three pages.
Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707>, last visited on Oct. 7, 2016, two pages.
Perez, M.T. et al. (Sep. 2002). "In Vivo Studies on Mouse Erythrocytes Linked to Transferrin," *IUBMB Life* 54(3):115-121.
Petition for Inter Partes Review of U.S. Pat. No. 8,892,190 (May 11, 2017), filed by Visionsense Corp., fifty four pages.
Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).
Phillips, R.P. et al. (1991). "Quantification of Diabetic Maculopathy by Digital Imaging of the Fundus," *Eye* 5(1):130-137.
Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.
Profio, A.E. et al. (Jul.-Aug. 1984). "Fluorometer for Endoscopic Diagnosis of Tumors," *Medical Physics* 11(4):516-520.
Profio, A.E. et al. (Jun. 1, 1991). "Endoscopic Fluorescence Detection of Early Lung Cancer," *Proc. SPIE* 1426:44-46.
Profio, A.E. et al. (Nov./Dec. 1979). "Laser Fluorescence Bronchoscope for Localization of Occult Lung Tumors," *Medical Physics* 6:523-525.
Profio, A.E. et al. (Sep.-Oct. 1986). "Digital Background Subtraction for Fluorescence Imaging," *Medical Physics* 13(5):717-721.

(56) References Cited

OTHER PUBLICATIONS

Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.
Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.
Raabe et al. (2009, e-published on Nov. 12, 2008). "Laser Doppler Imaging for Intraoperative Human Brain Mapping", *NeuroImage* 44:1284-1289.
Raabe, A. et al. (Jan. 2003). "Near-Infrared Indocyanine Green Video Angiography: A New Method for Intraoperative Assessment of Vascular Flow," Neurosurgery 52(1):132-139.
Rava, R.P. et al. (Jun. 1, 1991). "Early Detection of Dysplasia in Colon and Bladder Tissue Using Laser-Induced Fluorescence," *Proc. SPIE* 1426:68-78.
Razum, N. et al. (Nov. 1987). "Skin Photosensitivity: Duration and Intensity Following Intravenous Hematoporphyrin Derivatives, HpD and DHE, " *Photochemistry and Photobiology* 46(5):925-928.
Report on Observation by C2400-75i and ARGUS20 Under Low illumination conditions, Jan 17, 2008, six pages.
Request for Invalidation dated Jun. 29, 2007 for Japanese Patent No. JP-3881550, filed by Hamamatsu Photonics, Inc., eighty five pages, (with English Translation).
Reuthebuch, O et al. (Feb. 2004). "Novadaq Spy: Intraoperative Quality Assessment in Off Pump Coronary Artery Bypass Grafting," *Chest* 125(2):418-424.
Reuthebuch, O.T. et al. (May 2003). "Graft Occlusion After Deployment of the Symmetry Bypass System," *Ann. Thorac. Surg.* 75(5):1626-1629.
Richards-Kortum, R. et al. (Jun. 1991). "Spectroscopic Diagnosis of Colonic Dysplasia: Spectroscopic Analysis," *Biochemistry and Photobiology* 53(6):777-786.
Roberts, W.W. et al. (Dec. 1997). "Laparoscopic Infrared Imaging," *Surg. Endoscopy* 11(12):1221-1223.
Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.
Ropars, C. (ed.) et al. (1987). *Red Blood Cells as Carriers for Drugs. Potential therapeutic Applications*, Pergamon Press, Oxford, New York, pp. v-vii, (Table of Contents only), four.
Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.
Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.
Rossi, L. et al. (2001). "Erthrocyte-Mediated Delivery of Dexamethasone in Patients with Chronic Obstructive Pulmonary Disease," *Biotechnol. Appl. Biochem.* 33:85-89.
Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.
Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.
Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16.
Rübben, A. et al. (Mar. 1994). "Infrared Videoangiofluorography of the Skin with Indocyanine Green—Rat Random Cutaneous Flap Model and Results in Man," *Microvascular Research* 47(2):240-251.
Rubens, F.D. et al. (2002). "A New and Simplified Method for Coronary and Graft Imaging During CABG," *The Heart Surgery Forum* 5(2):141-144.
Sakatani, K. et al. (Nov. 1997). "Noninvasive Optical Imaging of the Subarachnoid Space and Cerebrospinal Fluid Pathways Based on Near Infrared Fluorescence," *J. Neurosurg.* 87(5):738-745.
Salmon E.D. et al.(Oct. 1994). "High Resolution Multimode Digital Imaging System for Mitosis Studies *in Vivo* and *in Vitro*," *Biol. Bull* 187(2):231-232.
Sato, M. et al., (1991). "Development of a Visualization Method for the Microcirculation of Deep Viscera Using an Infrared Intravital Microscope System," *Research on ME Devices and ME Technology*, five pages, (with English Translation).
Satpathy G.R. et al. (Oct. 2004, e-publication Aug. 7, 2004). "Loading Red Blood Cells with Trehalose: A Step Towards Biostabilization," *Cryobiology* 49(2):123-136.
Schaff, H.V. et al. (Oct. 15, 1996). "Minimal Thoracotomy for Coronary Artery Bypass: Value of Immediate Postprocedure Graft Angiography," *Supplement to Circulation* 94(8):I-51, (Abstract No. 0289), two pages.
Schellingerhout, D. et al. (Oct. 2000). "Quantitation of HSV Mass Distribution in a Rodent Brain Tumor Model," *Gene Therapy* 7(19):1648-1655.
Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.
Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.
Schneider Jr., H.C. et al. (Jan. 1975). "Fluorescence of Testicle, An Indication of Viability of Spermatic Cord After Torsion," *Urology* V(1):133-136.
Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.
Sekijima, M. et al. (Sep. 2004). "An Intraoperative Fluorescent Imaging System in Organ Transplantation," *Transplantation Proceedings* 36(7):2188-2190.
Serov, A. et al. (Mar. 1, 2002). "Laser Doppler Perfusion Imaging with a Complimentary Metal Oxide Semiconductor Image Sensor," *Optics Letters* 27(5):300-302.
Serov, A.N. et al. (Sep. 23, 2003). "Quasi-Parallel Laser Doppler Perfusion Imaging Using a CMOS Image Sensor," *Proc. SPIE* 5067:73-84.
Sezgin, M. et al. (Jan. 2004). "Survey Over Image Thresholding Techniques and Quantitative Performance Evaluation," *Journal of Electronic Imaging* 13(1):146-165.
Sherif, A. et al. (Sep. 2001). "Lymphatic Mapping and Detection of Sentinel Nodes in Patients with Bladder Cancer," *The Journal of Urology* 166(3):812-815.
Sheth, S.A. et al. (Apr. 22, 2004). "Linear and Nonlinear Relationships between Neuronal Activity, Oxygen Metabolism, and Hemodynamic Responses," *Neuron* 42(2):347-355.
Shoaib, T. et al. (Jun. 1, 2001). "The Accuracy of Head and Neck Carcinoma Sentinel Lymph Node Biopsy in the Clinically No Neck," *Cancer* 91(11):2077-2083.
Siemers, B.M. et al. (Nov. 2001). "The Acoustic Advantage of Hunting at Low Heights Above Water: Behaviorual Experiments on the European 'Trawling' *Bats Myotis Capaccinii, M Dasycneme* and *M. Daubentonii*," *J. Experimental Biol.* 204(Pt. 22):3843-3854.
Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.
Slakter, J.S. et al. (Jun. 1995). "Indocyanine-Green Angiography," *Current Opinion in Ophthalmology* 6(III):25-32.
Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

(56) References Cited

OTHER PUBLICATIONS

Soltesz, E.G. et al. (Jan. 2005). "Intraoperative Sentinel Lymph Node Mapping of the Lung Using Near-Infrared Fluorescent Quantum Dots," *Ann. Thorac. Surg.* 79(1):269-277.

Sony Corporation. The Sony U-Matic Videocassette Recorder, VO-9800, ten pages. (date not provided).

Staurenghi, G. et al. (Dec. 2001)."Combining Photodynamic Therapy and Feeder Vessel Photocoagulation: A Pilot Study," *Seminars in Ophthalmology* 16(4):233-236.

Stern, M.D. (Mar. 6, 1975). "*In Vivo* Evaluation of Microcirculation by Coherent Light Scattering," *Nature* 254(5495):56-58.

Still, J. et al. (Mar. 1999). "Evaluation of the Circulation of Reconstructive Flaps Using Laser-Induced Fluorescence of Indocyanine Green," *Ann. Plast. Surg.* 42(3):266-274.

Still, J.M. et al. (Jun. 2001). "Diagnosis of Burn Depth Using Laser-Induced Indocyanine Green Fluorescence: A Preliminary Clinical Trial," *Burns* 27(4):364-371.

Stoeckli, S.J. et al. (Sep. 2001). "Sentinel Lymph Node Evaluation in Squamous Cell Carcinoma of the Head and Neck," *Otolaryngol Head Neck Surg.* 125(3):221-226.

Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.

Sugi, K. et al. (Jan. 2003). "Comparison of Three Tracers for Detecting Sentinel Lymph Nodes in Patients with Clinical N0 Lung Cancer," *Lung Cancer* 39(1):37-40.

Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.

Suma, H. et al. (2000). "Coronary Artery Bypass Grafting Without Cardiopulmonary Bypass in 200 Patients," *J. Cardiol.* 36(2):85-90, (English Abstract only).

Summary of Invention Submitted to EPO, "Development of Novadaq SPY™Cardiac Imaging Invention," five pages. (date not provided).

Taggart, D.P. et al. (Mar. 2003). "Preliminary Experiences with a Novel Intraoperative Fluorescence Imaging Technique to Evaluate the Patency of Bypass Grafts in Total Arterial Revascularization," *Ann Thorac Surg.* 75(3):870-873.

Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.

Takahashi, M. et al. (Sep. 2004). "SPY™: An Innovative Intra-Operative Imaging System to Evaluate Graft Patency During Off-Pump Coronary Artery Bypass Grafting," *Interactive Cardio Vascular and Thoracic Surgery* 3(3):479-483.

Takayama, T. et al. (Apr. 1992). "Intraoperative Coronary Angiography Using Fluorescein Basic Studies and Clinical Application," *Vascular and Endovascular Surgery* 26(3):193-199.

Takayama, T. et al. (Jan. 1991). "Intraoperative Coronary Angiography Using Fluorescein" *The Annals of Thoracic Surgery* 51(1):140-143.

Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.

Tang, G.C. et al. (1989). "Spectroscopic Differences between Human Cancer and Normal Lung and Breast Tissues," *Lasers in Surgery and Medicine* 9(3):290-295.

Taylor, K.M. (Apr. 1998). "Brain Damage During Cardiopulmonary Bypass," *Annals of Thoracic Surgery* 65(4):S20-S26.

The American Heritage Medical Dictionary. "Perfuse." p. 401 (2008), three pages.

Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.

Torok, B. et al. (May 1996). "Simultaneous Digital Indocyanine Green and Fluorescein Angiography," *Klinische Monatsblatter Fur Augenheilkunde* 208(5):333-336, (Abstract only), two pages.

Tsutsumi, D. et al. "Moisture Detection of road surface using infrared camera," Reports of the Hokkaido Industrial Research Institute (No. 297), Issued on Nov. 30, 1998, two pages.

Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260.

Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.

Uren, R.F. (Jan. 2004). "Cancer Surgery Joins the Dots," *Nature Biotechnology* 22(1):38-39.

Valero-Cabré, A. et al. (Jan. 15, 2001). "Superior Muscle Reinnervation after Autologous Nerve Graft or Poly-L-Lactide-ϵ-Caprolactone (PLC) Tube Implantation in Comparison to Silicone Tube Repair," *Journal of Neuroscience Research* 63(2):214-223.

Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.

Verbeek, X. et al. (2001). "High-Resolution Functional Imaging With Ultrasound Contrast Agents Based on RF Processing in an In Vivo Kidney Experiment", *Ultrasound in Med. & Biol.* 27(2):223-233.

Wachi, A. et al. (Apr. 1995). "Characteristics of Cerebrospinal Fluid Circulation in Infants as Detected With MR Velocity Imaging," *Child's Nery Syst* 11(4):227-230.

Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.

Weinbeer, M. et al. (Nov. 25, 2013). "Behavioral Flexibility of the Trawling Long-Legged Bat, Macrophyllum Macrophyllum (Phyllostomidae)," *Frontiers in Physiology* 4(Article 342):1-11.

What is Perfusion? A Summary of Different Typed of Perfusion. (Sep. 1, 2004). Located at, <http://www.perfusion.com/cgi-bin/absolutenm/templates/articledisplay.asp?articleid=1548#. Vo8Hv02FPGj>, last visited on Jan. 7, 2016, two pages.

Wise, R.G. et al. (Nov. 2005). "Simultaneous Measurement of Blood and Myocardial Velocity in the Rat Heart by Phase Contrast MRI Using Sparse *q*-Space Sampling" *Journal of Magnetic Resonance Imaging* 22(5):614-627.

Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.

Wollert, H.G. et al. (Dec. 1989). "Intraoperative Visualization of Coronary Artery Fistula Using Medical Dye," *The Thoracic and Cardiovascular Surg.* 46(6):382-383.

Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.

Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.

Yamaguchi, S. et al. (Apr. 2005). "Evaluation of Skin Perfusion After Nipple-Sparing Mastectomy by Indocyanine Green Dye" *Journal of Saitama Medical University, Japan*, 32(2):45-50, (With English Abstract).

Yoneya, S. et al. (Jun. 1998). "Binding Properties of Indocyanine Green in Human Blood," *IOVS* 39(7):1286-1290.

Yoneya, S. et al. (Sep. 1993). "Improved Visualization of the Choroidal Circulation with Indocyanine Green Angiography," *Arch Opthalmol.* 111(9):1165-1166.

Young. I.T. et al. (1993). "Depth of Focus in Microscopy," SCIA '93, Proc. Of the 8th Scandinavian Conference on Image Analysis, Tromso, Norway, pp. 493-498, six pages.

Australian Examination Report No. 1 dated Jun. 26, 2018 for Australian Patent Application No. 2014408488, filed on Mar. 31, 2017, nine pages.

(56) References Cited

OTHER PUBLICATIONS

Australian Notice of Allowance dated Sep. 17, 2018 for Australian Patent Application No. 2015327665, filed on Mar. 23, 2017, three pages.
Canadian Notice of Allowance dated Jan. 4, 2018 for Canadian Application No. 2,750,760, filed on Jul. 25, 2008, one page.
Canadian Notice of Allowance dated Sep. 27, 2017 for Canadian Application No. 2,811,847, filed on Mar. 20, 2013, one page.
Canadian Office Action dated Feb. 27, 2017 for Canadian Application No. 2,750,760, filed on Jul. 25, 2011, three pages.
Canadian Office Action dated Feb. 13, 2018 for CA Application No. 2,963,450 filed on Apr. 3, 2017, three pages.
Canadian Office Action dated Feb. 28, 2018 for CA Application No. 2,963,987 filed on Mar. 27, 2017, five pages.
Canadian Office Action dated Jan. 19, 2017 for Canadian Application No. 2,914,778 filed on Dec. 8, 2015, four pages.
Canadian Office Action dated Mar. 16, 2016 for CA Application No. 2,750,760 filed on Jan. 23, 2009, five pages.
Canadian Office Action dated Nov. 28, 2017 for Canadian Application No. 2,914,778 filed on Dec. 8, 2015, six pages.
Canadian Office Action dated Oct. 25, 2016 for Canadian Patent Application No. 2,811,847, filed on Sep. 20, 2011, three pages.
Canadian Office Action dated Sep. 30, 2015 for CA Application No. 2,811,847, filed on Sep. 20, 2011, four pages.
Chinese Fifth Office Action dated Dec. 19, 2017 for Chinese Application No. 201180057244.8 filed on Sep. 20, 2011, eleven pages.
Chinese First Office Action dated Apr. 6, 2017 for Chinese Application No. 201510214021.8, filed on May 14, 2009, fifteen pages.
Chinese Fourth Office Action dated Mar. 13, 2017 for Chinese Application No. 201180057244.8 filed on Sep. 20, 2011, twenty pages.
Chinese Office Action dated Jul. 3, 2012, issued in counterpart Chinese Application No. 200980123414.0, eight pages.
Chinese Office Action dated May 23, 2013, issued in counterpart Chinese Application No. 200980123414.0, nineteen pages.
Chinese Office Action dated Nov. 12, 2015 for Chinese Patent Application No. 201180057244.8, filed on Sep. 20, 2010, five pages.
Chinese Second Office Action dated Feb. 8, 2018 for Chinese Application No. 201510214021.8, filed on May 14, 2009, seventeen pages.
Chinese Third Office Action dated Aug. 8, 2016 for Chinese Application No. 201180057244.8 filed on Sep. 20, 2011, eighteen pages.
European Decision in Opposition Proceeding Revoking (dated Jun. 10, 2010). European Patent No. 1 143 852, thirty pages.
European Decision of European Patent Office Technical Board of Appeal Revoking Counterpart Patent No. 1143852, dated Oct. 23, 2013.
European Decision to Grant dated Apr. 21, 2017 for EP Application No. 09732993.2, filed on Nov. 8, 2010, two pages.
European Decision to Grant dated Mar. 15, 2018 for EP Application No. 09739980.2 filed on Nov. 30, 2010, two pages.
European Extended Search Report dated Apr. 28, 2014 for EP Application No. 09 732 993.2, filed on Apr. 14, 2008, eight pages.
European Extended Search Report dated Feb. 22, 2012 for EP Application No. 09 704 642.9, filed on Jan. 25, 2008, fifteen pages.
European Extended Search Report dated Jan. 28, 2014 for EP Application No. 11 826 475.3, filed on Sep. 20, 2010, six pages.
European Extended Search Report dated Jun. 6, 2018 for EP Application No. 18166591.0 filed on Apr. 10, 2018, six pages.
European Extended Search Report dated May 23, 2018 for EP Application No. 14903635.2 filed on May 2, 2017, nine pages.
European Extended Search Report dated Oct. 14, 2015 for EP Application No. 13806313.6 filed on Jun. 20, 2013, nine pages.
European Extended Search Report dated Sep. 16, 2016 for EP Application No. 16183434.6 filed on Aug. 9, 2016, ten pages.
European Notice of Allowance dated Oct. 21, 2015 for EP Application No. 11 826 475.3, filed on Sep. 20, 2010, eight pages.

European Notice of Allowance dated Oct. 29, 2015 for EP Application No. 09 704 642.9, filed on Jan. 25, 2008, two pages.
European Office Action—Communication in pursuant to Article 94(3) EPC dated Mar. 9, 2016 for European Patent Application No. 09739980.2 filed May 1, 2009, five pages.
European Office Action—Communication Pursuant to Article 94(3) EPC dated Apr. 6, 2018 for EP Application No. 15188378.2 filed on Oct. 5, 2015, four pages.
European Office Action—Communication Pursuant to Article 94(3) EPC dated Aug. 31, 2017 for EP Application No. 09739980.2 filed on Nov. 30, 2010, four pages.
European Office Action—Communication pursuant to Article 94(3) dated May 27, 2016 for EP Application No. 15160177.0 filed on Aug. 11, 2000, five pages.
European Office Action—Communication Pursuant to Article 94(3) dated Sep. 21, 2017 for European Application No. 16163909.1 filed on Apr. 5, 2016, three pages.
European Office Action—Communication pursuant to Rules 70(2) and 70a(2) EPC dated May 15, 2014 in EP Application No. 09732993.2 , one page.
European Office Action—Communication pursuant to Rules 70(2) and 70a(2) EPC dated Nov. 14, 2016 in EP Application No. 16163909.1, two pages.
European Office Action—Communication Under Rule 71(3) EPC (Intention to Grant) dated Dec. 1, 2017 for European patent Application No. 09739980.2, filed on Nov. 30, 2010, seven pages.
European Office Action—Communication under Rule 71(3) EPC (Intention to Grant) dated Nov. 21, 2017 for European Patent Application No. 15160177.0, filed on Aug. 11, 2000, seven pages.
European Office Action dated Mar. 27, 2015 for EP Application No. 09 732 993.2, filed on Apr. 14, 2008, six pages.
European Opposition of European Patent No. EP1143852 lodged by Hamamatsu Photonics, Inc., Jul. 30, 2008.
European Partial Search Report dated Dec. 16, 2010 for European Application No. 10186218.3 filed on Aug. 11, 2000, seven pages.
European Partial Search Report dated Jan. 10, 2018 for EP Application No. 17171383.7 filed on May 16, 2017, eleven pages.
European Partial Search Report dated Jun. 11, 2014 for European Application No. 13178642.8, filed on May 1, 2009, five pages.
European Partial Search Report dated Jun. 28, 2016 for European Application No. 16163909.1 filed on Apr. 5, 2016, six pages.
European Summons to attend Oral Proceedings pursuant to Rule 115(1) EPC issued on Apr. 25, 2016 for European patent application No. 09732993.2, filed on Apr. 14, 2009, 5 pages.
European Summons to attend Oral Proceedings pursuant to Rule 115(1) EPC mailed on Dec. 16, 2016 for European patent application No. 15160177.0, filed on Aug. 11, 2000, seven pages.
European Supplemental Search Report dated Jul. 6, 2004 for EP Application No. 00955472.6 filed on Aug. 11, 2000, five pages.
Indian Examination Report dated Jan. 16, 2018 for Indian Application No. 2993/DELNP/2011, filed on Apr. 25, 2011, eleven pages.
Indian Examination Report dated Jul. 28, 2017 for Indian Application No. 1983/MUMNP/2007, filed on Nov. 27, 2007, seven pages.
Indian Examination Report dated Sep. 22, 2016 for Indian Application No. 7566/DELNP/2010, filed on Oct. 27, 2010, nine pages.
International Preliminary Examination Report completed on Jul. 1, 2001 for PCT/US00/22088, filed on Aug. 11, 2000, three pages.
International Preliminary Report on Patentability dated Apr. 4, 2017 for PCT Application No. PCT/CA2015/050973 filed on Sep. 28, 2015, six pages.
International Search Report and the Written Opinion of the International Searching Authority, or the Declaration dated Apr. 3, 2008 for PCT/US07/77892, filed on Sep. 7, 2007, ten pages.
International Search Report and Written Opinion dated Jul. 29, 2009 for PCT/US2009/043975 filed on May 14, 2009, eleven pages.
International Search Report and Written Opinion dated Oct. 24, 2017 for PCT Application No. PCT/CA2017/050564 filed on May 10, 2017, fourteen pages.
International Search Report dated Dec. 3, 2015 for PCT Application No. PCT/CA2015/050973 filed on Sep. 28, 2015, three pages.
International Search Report dated Jul. 4, 2008 for PCT Patent Application No. PCT/US2007/080847, filed on Oct. 9, 2007, three pages.

(56) References Cited

OTHER PUBLICATIONS

International Search Report dated Dec. 3, 2009 for PCT Patent Application No. PCT/IB2009/005700, filed on Apr. 14, 2009, three pages.
International Search Report dated Feb. 1, 2012 for PCT Patent Application No. PCT/IB2011/002381, filed on Sep. 20, 2011, five pages.
International Search Report dated Jan. 22, 2014 for PCT Application No. PCT/IB2013/001934, filed on Jun. 20, 2013, four pages.
International Search Report dated Jun. 2, 2009 for PCT Application No. PCT/EP2008/008547, filed on Oct. 9, 2008, five pages.
International Search Report dated Jun. 8, 2009 for PCT Patent Application No. PCT/CA2009/000073, filed on Jan. 23, 2009, three pages.
International Search Report dated Oct. 18, 2000 for PCT Application No. PCT/US2000/22088, filed on Aug. 11, 2000, one page.
International Search Report dated Sep. 11, 2009 for Application No. PCT/US2009/042606 filed on May 1, 2009, five pages.
Invitation to Pay Additional Fees and, Where Applicable, Protest Fee dated Jul. 4, 2017 for PCT/CA2017/050564, filed on May 10, 2017, two pages.
Japanese Final Office Action dated Feb. 5, 2018 for Japanese Patent Application No. 2016-014503, filed on Jan. 28, 2016, six pages.
Japanese First Office Action dated Feb. 1, 2016 for Japanese Patent Application No. 2015-517876 filed Jun. 20, 2013, eight pages.
Japanese First Office Action dated Jul. 28, 2017 for Japanese Patent Application No. 2016- 203798 filed Oct. 17, 2016, four pages.
Japanese Notice of Allowance dated Jun. 8, 2018 for Japanese Patent Application No. 2016-203798 filed Oct. 17, 2016, six pages.
Japanese Notice of Allowance dated Sep. 16, 2016 for Japanese Patient Application No. 2015-517876 filed on Jun. 20, 2013, six pages.
Japanese Notice of Allowance dated Sep. 25, 2017 for Japanese Patent Application No. 2013-529729, filed on Mar. 21, 2013, six pages.
Japanese Office Action dated Apr. 1, 2016 for Japanese Patent Application No. 2013-529729, filed on Mar. 21, 2013, seven pages, (with English Translation).
Japanese Office Action dated Aug. 20, 2018 for Japanese Patent Application No. 2017- 205499, filed on Nov. 24, 2017, six pages.
Japanese Office Action dated Jul. 30, 2013, issued in counterpart Japanese Application No. 2011-504574, filed Apr. 14, 2009, six pages.
Japanese Office Action dated Mar. 3, 2017 for Japanese Patent Application No. 2016-014503, filed on Jan. 28, 2016, ten pages.
Japanese Office Action dated Mar. 19, 2018 for Japanese Application No. 2017-518785 filed on Apr. 7, 2017, eight pages.
Japanese Office Action dated Mar. 31, 2017 for Japanese Patent Application No. 2013-529729, filed on Mar. 21, 2013, eleven pages.
Japanese Office Action dated May 7, 2018 for Japanese Patent Application No. 2017-516925 filed on Mar. 28, 2017, four pages.
Japanese Office Action dated Sep. 14, 2015 for Japanese Patent Application No. 2011-504574, filed on Apr. 14, 2009, three pages.
Korean Notice of Allowance dated Apr. 27, 2017 for Korean Patent Application No. 10-2016-7007994, filed on Mar. 25, 2016, three pages, (with English Translation).
Korean Notice of Allowance dated Apr. 29, 2016 for Korean Patent Application No. 10-2010-7024977, filed on Apr. 14, 2009, three pages.
Korean Office Action dated Apr. 17, 2018 for Korean Patent Application No. Oct. 2017-7012463, filed on May 8, 2017, six pages.
Korean Office Action dated Nov. 30, 2015 for Korean Patent Application No. 10-2010-7024977, filed on Apr. 14, 2009, two pages.
Korean Patent Office Action dated Jun. 25, 2014 in Korean Patent Application No. 10-2013-7035027, filed on May 14, 2009, fifteen pages.
Mexican Office Action dated May 30, 2013, issued in counterpart Mexican Application No. MX/a/2010/011249.

Novadaq Technologies Inc.'s Preliminary Response filed on Aug. 23, 2017 to Petition for Inter Partes Review of U.S. Pat. No. 8,892,190 sixty one pages.
Russian Decision on Grant dated Jul. 29, 2013, issued in counterpart Russian Application No. 2011111078.14, five pages.
Russian Office Action dated Mar. 29, 2013, issued in counterpart Russian Application No. 2011111078.14, three pages.
Translation of Decision of Japanese Patent Office Trial Board revoking Counterpart Patent No. U.S. Pat. No. 3,881,550, twenty six pages. (date not provided).
U.S. Final Office Action dated Apr. 2, 2013 for U.S. Appl. No. 13/419,368, filed Mar. 13, 2012, five pages.
U.S. Final Office Action dated Apr. 4, 2017 for U.S. Appl. No. 12/933,477, filed Sep. 20, 2010, twelve pages.
U.S. Final Office Action dated Apr. 10, 2008 for U.S. Appl. No. 11/106,154, filed Apr. 14, 2005, six pages.
U.S. Final Office Action dated Apr. 12, 2017 for U.S. Appl. No. 14/543,429, filed Nov. 17, 2014, nine pages.
U.S. Final Office Action dated Apr. 20, 2016 for U.S. Appl. No. 14/543,429, filed Nov. 17, 2014, seven pages.
U.S. Final Office Action dated Apr. 27, 2011 for U.S. Appl. No. 11/515,419, filed Sep. 1, 2006, nine pages.
U.S. Final Office Action dated Aug. 10, 2012 for U.S. Appl. No. 11/912,877, filed Aug. 13, 2008, ten pages.
U.S. Final Office Action dated Dec. 4, 2014 for U.S. Appl. No. 12/776,835, filed May 10, 2010, thirteen pages.
U.S. Final Office Action dated Dec. 31, 2015 for U.S. Appl. No. 14/177,050, filed Feb. 10, 2014, eighteen pages.
U.S. Final Office Action dated Feb. 1, 2013 for U.S. Appl. No. 12/776,835, filed May 10, 2010, thirteen pages.
U.S. Final Office Action dated Feb. 4, 2015 for U.S. Appl. No. 13/314,418, filed Dec. 8, 2011, six pages.
U.S. Final Office Action dated Feb. 13, 2015 for U.S. Appl. No. 14/543,429, filed Nov. 17, 2014, six pages.
U.S. Final Office Action dated Feb. 18, 2010 for U.S. Appl. No. 11/106,154, filed Apr. 14, 2005, six pages.
U.S. Final Office Action dated Jul. 9, 2015 for U.S. Appl. No. 14/543,356, filed Nov. 17, 2014, eight pages.
U.S. Final Office Action dated Jul. 21, 2016 for U.S. Appl. No. 14/543,356, filed Nov. 17, 2014, seven pages.
U.S. Final Office Action dated Jun. 1, 2015 for U.S. Appl. No. 14/543,429, filed Nov. 17, 2014, nine pages.
U.S. Final Office Action dated Jun. 13, 2014 for U.S. Appl. No. 12/776,835, filed May 10, 2010, thirteen pages.
U.S. Final Office Action dated Jun. 25, 2014 for U.S. Appl. No. 12/933,477, filed Sep. 20, 2010, fifteen pages.
U.S. Final Office Action dated Mar. 20, 2017 for U.S. Appl. No. 14/177,050, filed Feb. 10, 2014, twenty three pages.
U.S. Final Office Action dated Mar. 28, 2013 for U.S. Appl. No. 12/063,349, filed May 12, 2010, twenty pages.
U.S. Final Office Action dated May 29, 2013 for U.S. Appl. No. 12/933,477, filed Sep. 20, 2010, twelve pages.
U.S. Final Office Action dated Nov. 6, 2013 for U.S. Appl. No. 13/419,368, filed Mar. 13, 2012, five pages.
U.S. Final Office Action dated Oct. 7, 2011 for U.S. Appl. No. 11/851,312, filed Sep. 6, 2007, ten pages.
U.S. Final Office Action dated Sep. 13, 2011 for U.S. Appl. No. 11/106,154, filed Apr. 14, 2005, five pages.
U.S. Final Office Action dated Sep. 17, 2014 for U.S. Appl. No. 11/515,419, filed Sep. 1, 2006, eleven pages.
U.S. Final Office Action dated Sep. 17, 2015 for U.S. Appl. No. 12/933,477, filed Sep. 20, 2010, six pages.
U.S. Final Office Action dated Sep. 23, 2004 for U.S. Appl. No. 09/744,034, filed Apr. 27, 2001, seven pages.
U.S. Final Office Action dated Sep. 29, 2016 for U.S. Appl. No. 13/922,996, filed Jun. 20, 2013, fourteen pages.
U.S. Non-Final Office Action dated Apr. 1, 2015 for U.S. Appl. No. 12/933,477, filed Sep. 20, 2010, fourteen pages.
U.S. Non-Final Office Action dated Apr. 26, 2012 for U.S. Appl. No. 12/776,835, filed on May 10, 2010, nine pages.
U.S. Non-Final Office Action dated Apr. 28, 2010 for U.S. Appl. No. 11/946,672, filed Nov. 28, 2007, nine pages.

(56) References Cited

OTHER PUBLICATIONS

U.S. Non-Final Office Action dated Aug. 10, 2016 for U.S. Appl. No. 14/177,050, filed Feb. 10, 2014, twenty pages.
U.S. Non-Final Office Action dated Aug. 29, 2014 for U.S. Appl. No. 12/063,349, filed May 12, 2010, nineteen pages.
U.S. Non-Final Office Action dated Dec. 16, 2016 for U.S. Appl. No. 14/868,369, filed Sep. 28, 2015, seven pages.
U.S. Non-Final Office Action dated Dec. 20, 2013 for U.S. Appl. No. 12/933,477, filed Sep. 20, 2010, thirteen pages.
U.S. Non-Final Office Action dated Dec. 30, 2010 for U.S. Appl. No. 11/106,154, filed Apr. 14, 2005, six pages.
U.S. Non-Final Office Action dated Feb. 1, 2011 for U.S. Appl. No. 11/851,312, filed Sep. 6, 2007, seven pages.
U.S. Non-Final Office Action dated Feb. 5, 2016 for U.S. Appl. No. 14/543,356, filed Nov. 17, 2014, seven pages.
U.S. Non-Final Office Action dated Jan. 8, 2018 for U.S. Appl. No. 15/077,677, filed Mar. 22, 2016, nine pages.
U.S. Non-Final Office Action dated Jan. 9, 2009 for U.S. Appl. No. 11/106,154, filed Apr. 14, 2005, six pages.
U.S. Non-Final Office Action dated Jan. 22, 2014 for U.S. Appl. No. 11/851,312, filed Sep. 6, 2007, ten pages.
U.S. Non-Final Office Action dated Jan. 27, 2012 for U.S. Appl. No. 11/912,877, filed Aug. 13, 2008, eleven pages.
U.S. Non-Final Office Action dated Jan. 31, 2018 for U.S. Appl. No. 15/799,727 filed Oct. 31, 2017, seven pages.
U.S. Non-Final Office Action dated Jul. 2, 2015 for U.S. Appl. No. 14/177,050, filed Feb. 10, 2014, nineteen pages.
U.S. Non-Final Office Action dated Jul. 8, 2014 for U.S. Appl. No. 13/314,418, filed Dec. 8, 2011, seven pages.
U.S. Non-Final Office Action dated Jul. 22, 2015 for U.S. Appl. No. 13/314,418, filed Dec. 8, 2011, six pages.
U.S. Non-Final Office Action dated Jun. 11, 2013 for U.S. Appl. No. 11/515,419, filed Sep. 1, 2006, eleven pages.
U.S. Non-Final Office Action dated Jun. 28, 2012 for U.S. Appl. No. 12/063,349, filed May 12, 2010, seventeen pages.
U.S. Non-Final Office Action dated Mar. 6, 2007 for U.S. Appl. No. 11/106,154, filed Apr. 14, 2005, eight pages.
U.S. Non-Final Office Action dated Mar. 10, 2004 for U.S. Appl. No. 09/744,034, filed Apr. 27, 2001, seven pages.
U.S. Non-Final Office Action dated Mar. 13, 2015 for U.S. Appl. No. 14/543,356, filed Nov. 17, 2014, eight pages.
U.S. Non-Final Office Action dated May 6, 2015 for U.S. Appl. No. 12/063,349, filed May 12, 2010, seventeen pages.
U.S. Non-Final Office Action dated May 21, 2015 for U.S. Appl. No. 13/922,996, filed Jun. 20, 2013, fourteen pages.
U.S. Non-Final Office Action dated Nov. 9, 2015 for U.S. Appl. No. 14/177,045, filed Feb. 10, 2014, seven pages.
U.S. Non-Final Office Action dated Nov. 18, 2016 for U.S. Appl. No. 12/933,477, filed Sep. 20, 2010, six pages.
U.S. Non-Final Office Action dated Nov. 27, 2015 for U.S. Appl. No. 14/543,429, filed Nov. 17, 2014, six pages.
U.S. Non-Final Office Action dated Oct. 3, 2013 for U.S. Appl. No. 12/776,835, filed May 10, 2010, twelve pages.
U.S. Non-Final Office Action dated Oct. 12, 2016 for U.S. Appl. No. 14/543,429, filed Nov. 17, 2014, nine pages.
U.S. Non-Final Office Action dated Oct. 13, 2017 for U.S. Appl. No. 13/922,996, filed Jun. 20, 2013, seventeen pages.
U.S. Non-Final Office Action mdated Oct. 26, 2017 for U.S. Appl. No. 14/543,429, filed Nov. 17, 2014, nine pages.
U.S. Non-Final Office Action dated Oct. 28, 2016 for U.S. Appl. No. 14/543,356, filed Nov. 17, 2014, eight pages.
U.S. Non-Final Office Action dated Sep. 5, 2012 for U.S. Appl. No. 12/933,477, filed Sep. 20, 2010, seven pages.
U.S. Non-Final Office Action dated Sep. 15, 2010 for U.S. Appl. No. 11/106,154, filed Apr. 14, 2005, six pages.
U.S. Non-Final Office Action dated Sep. 27, 2017 for U.S. Appl. No. 14/177,050, filed Feb. 10, 2014, twenty two pages.
U.S. Non-Final Office Action dated Sep. 30, 2010 for U.S. Appl. No. 11/515,419, filed Sep. 1, 2006, eleven pages.
U.S. Notice of Allowance dated Apr. 17, 2014 for U.S. Appl. No. 13/419,368, filed Mar. 13, 2012, five pages.
U.S. Notice of Allowance dated Aug. 7, 2014 for U.S. Appl. No. 13/850,063, filed Mar. 25, 2013, nine pages.
U.S. Notice of Allowance dated Dec. 2, 2016 for U.S. Appl. No. 14/598,832, filed Jan. 16, 2015, seven pages.
U.S. Notice of Allowance dated Dec. 6, 2017 for U.S. Appl. No. 15/476,290, filed Mar. 31, 2017, nine pages.
U.S. Notice of Allowance dated Jul. 12, 2017 for U.S. Appl. No. 14/868,369, filed Sep. 28, 2015, nine pages.
U.S. Notice of Allowance dated Jul. 13, 2016 for U.S. Appl. No. 14/598,832, filed Jan. 16, 2015, seven pages.
U.S. Notice of Allowance dated Jun. 15, 2018 for U.S. Appl. No. 11/515,419, filed Sep. 1, 2006, five pages.
U.S. Notice of Allowance dated Mar. 7, 2005 for U.S. Appl. No. 09/744,034, filed Apr. 27, 2001, five pages.
U.S. Notice of Allowance dated Mar. 15, 2016 for U.S. Appl. No. 14/598,832, filed Jan. 16, 2015, seven pages.
U.S. Notice of Allowance dated Mar. 29, 2018 for U.S. Appl. No. 14/177,050, filed Feb. 10, 2014, ten pages.
U.S. Notice of Allowance dated May 26, 2016 for U.S. Appl. No. 14/177,045, filed Feb. 10, 2014, eight pages.
U.S. S Notice of Allowance dated Nov. 25, 2015 for U.S. Appl. No. 14/598,832, filed Jan. 16, 2015, seven pages.
U.S. Notice of Allowance dated Nov. 30, 2010 for U.S. Appl. No. 11/946,672, filed Nov. 28, 2007, six pages.
U.S. Notice of Allowance dated Oct. 4, 2013 for U.S. Appl. No. 11/912,877, filed Aug. 13, 2008, nine pages.
U.S. S Notice of Allowance dated Oct. 6, 2014 for U.S. Appl. No. 13/419,368, filed Mar. 13, 2012, five pages.
U.S. Notice of Allowance dated Oct. 16, 2014 for U.S. Appl. No. 13/850,063, filed Mar. 25, 2013, eight pages.
U.S. Notice of Allowance dated Oct. 18, 2012 for U.S. Appl. No. 12/841,659, filed Jul. 22, 2010, seven pages.
U.S.otice of Allowance dated Sep. 6, 2018 for U.S. Appl. No. 12/776,835, filed May 10, 2010, five pages.
U.S. Notice of Allowance dated Sep. 6, 2018 for U.S. Appl. No. 13/922,996, filed Jun. 20, 2013, nine pages.
U.S. Notice of Allowance dated Sep. 11, 2018 for U.S. Appl. No. 15/799,727 filed Oct. 31, 2017, eight pages.
U.S. Restriction Requirement dated Jun. 26, 2017 for U.S. Appl. No. 15/077,677, filed Mar. 22, 2016, seven pages.
Written Opinion of the International Searching Authority dated Jul. 4, 2008 for PCT Patent Application No. PCT/US2007/080847, filed on Oct. 9, 2007, six pages.
Written Opinion of the International Searching Authority dated Dec. 3, 2009 for PCT Patent Application No. PCT/IB2009/005700, filed on Apr. 14, 2009, six pages.
Written Opinion of the International Searching Authority dated Dec. 3, 2015 for PCT Patent Application No. PCT/CA2015/050973 filed on Sep. 28, 2015, five pages.
Written Opinion of the International Searching Authority dated Feb. 1, 2012 for PCT Patent Application No. PCT/IB2011/002381, filed on Sep. 20, 2011, four pages.
Written Opinion of the International Searching Authority dated Jan. 22, 2014 for PCT Patent Application No. PCT/IB2013/001934, filed on Jun. 20, 2013, six pages.
Written Opinion of the International Searching Authority Jun. 2, 2009 for PCT Patent Application No. PCT/EP2008/008547, filed on Oct. 9, 2008, eleven pages.
Written Opinion of the International Searching Authority dated Jun. 8, 2009 for PCT Patent Application No. PCT/CA2009/000073, filed on Jan. 23, 2009, four pages.

\* cited by examiner

Figure 2: Intraoperative image of left inguinal lymph nodes

PRE-AND-INTRA-OPERATIVE LOCALIZATION OF PENILE SENTINEL NODES

CROSS-REFERENCES TO RELATED APPLICATIONS

This application is a continuation of U.S. application Ser. No. 11/851,312, filed Sep. 6, 2007, which claims the benefit of U.S. Provisional Application No. 60/843,175, filed Sep. 7, 2006, each of which are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

A variety of medical techniques suitable for imaging biological tissues and organs are known. These include traditional x-rays, ultra-sound, magnetic resonance imaging, and computerized tomography.

A variety of dyes useful for medical imaging have been described, including radio opaque dyes, fluorescent dyes, and colorimetric dyes (see e.g., U.S. Pat. Nos. 5,699,798; 5,279,298; 6,351,663). Imaging techniques and systems using fluorescent dyes have been described for the heart and eye (see, e.g., U.S. Pat. No. 5,279,298). Some dyes can serve both an imaging function and a therapeutic function (see, e.g. U.S. Pat. No. 6,840,933). Some specific neuronal imaging agents have been used to visualize tissue in the central nervous system. Tracer uptake and transport has been demonstrated in different studies using various routes of administration including antegrade, retrograde and combined routes (Jones et al. 1978, *Annu Rev Neurosci.*, 1:215; Rosina A., 1982, *Neurosci Lett.* 33(3):217; Illing R B, et al., 1985, *Neuroscience* 14(2):455; Sloniewski P, et al., 1985, *Neurosci Lett.* 60(2):189; and Schmued et al., 1986, *Brain Res.* 377(1):147). After appropriate time for endo/pinocytosis, perineural lymphatic and axonal transport, which generally measures 0.5-2 mm per hour, tracers were visually detected using ultraviolet or visible light (Bentivoglio et al., 1980, *Neurosci Lett.* 18(1):19; Minciacchi D et al., 1991, *J Neurosci Methods.* 38(2-3):183). Tracers such as Indocyanine Green, Fast Blue, and Fluorogold, have been used in mammals without evidence of neuronal toxicity several months after the treatment (Thielert et al., 1993, *J Comp Neurol.* 337(1):113; Yeterian et al., 1994, *Exp Brain Res.* 99(3):383; vogt Weisenhorn et al., 1995, *J Comp Neurol.* 362(2):233). Marangos et al. labeled the auditory nerve using Fluorogold and Fast Blue in rats and monkeys by suctioning out perilymph and filling the cochlea with neuronal tracers to identify the nerve and cochlear brain stem nucleus for the positioning of electrodes for an auditory neuroprosthesis (Marangos N, et al., 2001, *Hear Res.* 162(1-2):48).

According to the American Cancer Society, only some 1,500 cases are diagnosed a year in the U.S., accounting for only 0.2% of cancers in men in the U.S. Although penile cancer is relatively uncommon among American and European men, it is much more common in Africa and South America, where it accounts for 10% of all male cancers. While definitive causes of penile cancer are not known, there are some known risk factors. One such risk factor is infection with human papillomavirus. In a report available on-line as of this writing, Senba et al., *J Med Virol.* 2006, 78(10):1341-6, reported the detection of human papillomavirus DNA in 80% of 65 samples of penile cancer from Thai men, with HPV-18 being the most prevalent. Another, in uncircumcised males, is the buildup of secretions under the foreskin.

According to the American Cancer Society, some 95% of penile cancers are squamous cell carcinomas and usually develop on the foreskin (if the male is uncircumcised) or the glans. Typically, the patient presents with a rash, bumps, ulcer or discharge, and the cancer is diagnosed by microscopic examination of biopsied tissue. Lymph node metastasis is a crucial prognostic factor in penile cancer. About 50% of patients with palpable lymph nodes will have metastases, and about 20% of patients without enlarged lymph nodes will have lymphatic spread (Hardner, G J, *J Urol*, 108:428ff (1972); Kossow, J H, *Urology*, 2:169ff (1973); McDougal, W S, *J Urol* 136:38ff (1986)). Successful sentinel lymph node dissection (SLND) is predicated on precise detection of the lymphatic drainage into sentinel nodes. According to the National Cancer Institute, when diagnosed early (stage 0, stage I, and stage II), penile cancer is highly curable, but curability decreases sharply for stage III and stage IV. Criteria for staging penile cancer are known in the art, and set forth at, e.g., Penis: American Joint Committee on Cancer, *AJCC Cancer Staging Manual*, 6th Ed., Springer, NY N.Y., 2002, pp. 302-8.

Unfortunately, there is significant anatomical variation in penile lymph node drainage as well as in sentinel lymph node position. In multiple cases, current dye or radionuclide lymphatic tracing methods result in identification of sentinel and some of the metastatic lymph nodes (Cabanas, R M, *Urol Clin N Am* 19:267ff (1992); Lynch, D F, Jr: *AUA update series*, 16:256 (1997)). Nevertheless these procedures are difficult, time-consuming, expensive and have low sensitivity, especially when used with methylene blue. If sentinel nodes are found without metastases this would obviate unnecessary removal of noninvolved nodes as seen in 90-95% of superficial lesions, 50-60% of T2 lesions, and 10-20% of T2b and T3 lesions (Horenblas et al., *J Urol* 155:1239-1243 (1994)). The presence of metastases will be followed by complete lymph node dissection. Current practice is to remove all inguinal or ilioinguinal lymph nodes in penile cancer surgeries, resulting in significant morbidity in more than 30% of the patients. Multiple methods, such as the use of radioactive tracers, have been used in the hope of improving the detection of sentinel nodes, see, e.g., Brennhovd et al., Sentinel node procedure in low-stage/low-grade penile carcinomas, *Scand J Urol Nephrol.* 2006; 40(3):204-7, but no method has yet emerged as a standard.

Accordingly, a need exists for improved methods of locating sentinel lymph nodes for persons with penile cancer. The present invention fills these and other needs.

BRIEF SUMMARY OF THE INVENTION

The invention provides methods of localizing before or during a surgical operation a lymph node draining a penile tumor having edges and a base in a subject, comprising, about 10 minutes to about 24 hours prior to the surgical operation, injecting the edges or the base of the tumor of the subject with a dye which fluoresces at an emission wavelength when the dye is contacted with an excitation wavelength; exposing the lymph node to illumination comprising the excitation wavelength, thereby causing the fluorescent dye to fluoresce; and, detecting the fluorescence of the dye, thereby localizing the lymph node. In some embodiments, the lymph node is a sentinel lymph node. In some embodiments, the dye is injected into the edges of the tumor. In some embodiments, the dye is injected into the base of the tumor. In some embodiments, the lymph node is visualized on a image display. In some embodiments, the exposure of the lymph node to excitation wavelength is by a laparoscopic instrument. In some embodiments, the dye is a dye which fluoresces when exposed to near infrared light. In some embodiments, the dye is a tricarbocyanine dye or an analog thereof. In some embodiments, the tricarbocyanine dye is indocyanine green. In some embodiments, the subject is a human. In some embodiments, the dye is injected between about 10 minutes and 12 hours before the surgical operation. In some embodiments, the dye is injected between about 1 hour and about 6 hours before the surgical operation. In some embodiments, the dye is injected between about 1 hour and about 2 hours before the surgical operation. In some embodiments, the steps of exposing the lymph node to illumination comprising the excitation wavelength, thereby causing the fluorescent dye to fluoresce; and detecting the fluorescence of the dye, thereby localizing the lymph node, are performed during the surgical operation. In some embodiments, the surgical operation is a laparoscopic operation.

BRIEF DESCRIPTION OF THE DRAWINGS

FIG. 2 shows an intraoperative image of inguinal lymph nodes first detected by near infrared fluorescence (NIRF) through the body wall of a rat in which indocyanine green had been injected into the cavernous bodies of the penis. Arrows indicate the lymphatics and the lymph nodes.

DETAILED DESCRIPTION OF THE INVENTION

Figure 1:
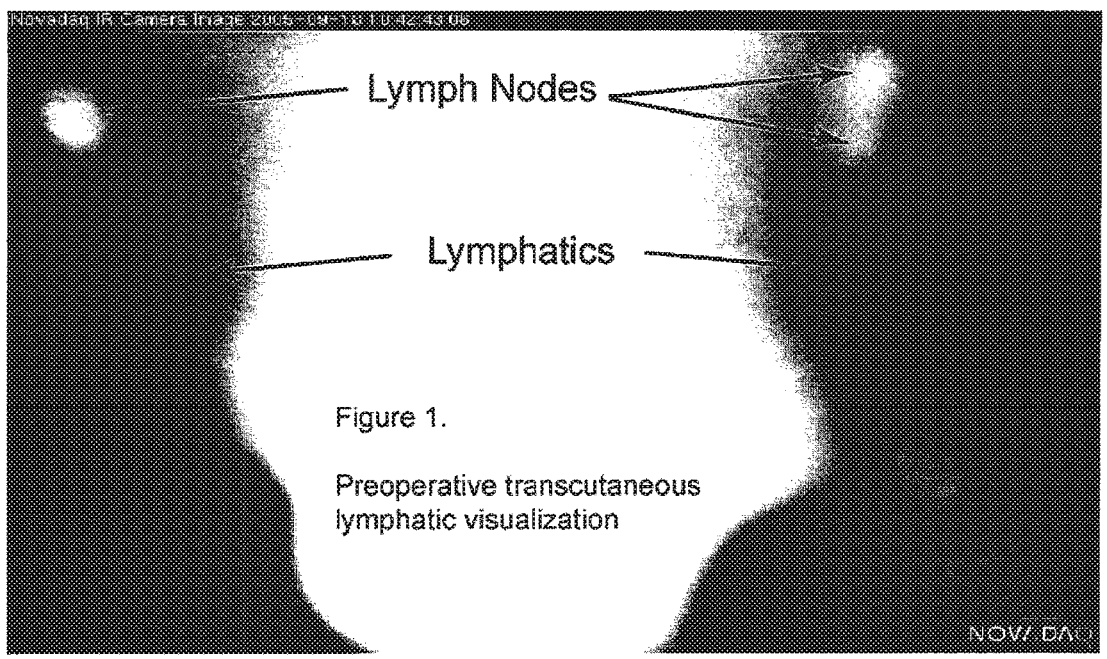
FIG. 1 shows detection of inguinal lymph nodes by near infrared fluorescence (NIRF) through the body wall of a rat in which indocyanine green had been injected into the cavernous bodies of the penis. Arrows indicate the lymphatics and the lymph nodes.

Lymph nodes that receive the lymph from a particular organ or region of the body are considered to "drain" that organ or region. As set forth in the Background, various techniques and agents have been used to try to detect the lymph nodes draining penile cancers. Unfortunately, all suffer from various problems, such as exposing the patient to radioactivity, and none have emerged as a standard of care.

It will be appreciated that penile tumors can spread in two planes: both laterally along the surface of the penis and vertically, into the penis. Thus, a tumor can be considered to have both edges, defining the lateral borders of the tumor, and a base, defining the depth to which the tumor has invaded into the tissue and structures of the penis. Surprisingly, it has now been discovered that the lymph nodes draining the cancer can be localized and visualized by injecting the edges or base of the tumor, or preferably, both, with a non-toxic, fluorescent dye. Thus, if the tumor is located on the glans of the penis, the injections will be in the glans, while a tumor in the prepuce (more familiarly known as the foreskin), the injections will be into the prepuce. For tumors that have invaded into one or both of the corpus cavernosum, injections are made into the base of the tumor in the affected corpus cavernosum. (As persons of skill are aware, "corpus cavernosum" is the singular form and "corpora cavernosa" is the plural form. For convenience, the corpora cavernosa will sometimes be referred to herein as the "cavernous bodies." Also for convenience of reference, the ability to locate and visualize nodes can be referred to as "localizing" the nodes.)

The dye injections are typically about 30 to 300 µl each, more preferably about 50 to about 200 µl, still more preferably about 60 to about 175 µl, more preferably about 75 to about 150 µl, more preferably about 90 to about 125 µl each, more preferably about 100 µl, and most preferably 100 µl each, with "about" in this context meaning plus or minus 15 µl. For a small tumor, as few as two shots around the edges or base of the tumor will be sufficient. Larger tumors will typically take 5 shots dispersed around the edges and base. Larger tumors with deeper invasion into the tissues and cavernous bodies could require up to 10 injections. Urologic surgeons are considered to be familiar with the criteria for staging penile cancers, which are based in part on the extent to which the tumor has invaded the tissue; selecting a suitable number of injections for tumors of different sizes is considered to be within the skill of the practitioner.

In studies in an animal model, injection of an exemplar fluorescent dye, indocyanine green (ICG) resulted in the ability to visualize the lymph nodes in as little as 10 minutes after injection. Thus, if desired, dye injections can be made as soon as the patient is in the operating room and under anesthesia. To minimize the duration of use of the operating room and surgical team, however, the injections will more typically be given pre-operatively. Patients are, typically prepared for penile cancer surgery in a pre-anesthesia room an hour or two before the surgery, during which time they are given mild sedation or a calming medication. Conveniently, the dye injections are made after the sedative has taken effect to reduce the patient's discomfort at receiving small penile injections.

In animal studies, lymph nodes could be seen through the body wall for days after injection; however, in the context of detecting and visualizing sentinel nodes, periods as long as 24 hours may permit the dye to disperse to more distal lymph nodes. Thus, to facilitate identifying the sentinel nodes rather than more distal lymph nodes to which the dye may disperse, it is preferable to administer the dye 12 hours or less before the surgical operation, with 11, 10, 9, 8, 7, 6, 5, 4, 3, and 2 hours being successively more preferred. In still more preferred embodiments, the dye is administered about 1 to 2 hours before the operation, with "about" in this context meaning one-half hour on either side of the designated time. Most preferably, the dye is injected about 1 hour before the operation, with "about" in this context meaning plus or minus 15 minutes, permitting the dye to reach the sentinel nodes while minimizing the dispersion to more distal nodes.

FIG. 1 shows fluorescence in a rat injected in the cavernous bodies with ICG. Arrows point to the lymphatic channels and to the lymph nodes. More than one sentinel nodes were visualized in two rats. No fluorescence was seen in control animals injected with saline. Intraoperative observations confirmed the preoperative localization of the inguinal nodes. All lymph nodes were confirmed by conventional histological review. FIG. 2 shows an intraoperative image of left inguinal lymph nodes following injection of ICG into the cavernous bodies.

It is understood that fluorescent dyes have a particular excitation wavelength which causes the dye to fluoresce and emit light of a particular emission wavelength. As persons of skill are aware, there is a considerable literature on the characteristics of different dyes, including their excitation wavelength and emission wavelength.

The methods described herein are suitable for use in mammals. Examples of mammals for which the techniques can be used include, but are not limited to, non-human primates, dogs, cats, sheep, cows, pigs, horses, and rabbits. The methods are particularly useful in visualizing lymph nodes in humans, and particularly the lymph nodes draining the penis in humans.

Penile Anatomy

It is assumed that urologic surgeons and other persons of skill are well familiar with the anatomy of the penis, the prostate, and the surrounding areas, and that no detailed discussion is needed here. For purposes of the present discussion, it is noted that the penis can be thought of as comprising three cylinders. Two, the corpora cavernosa, are disposed on either side of the penis, and make up the bulk of the penis. The third, the corpus spongiosum, which contains the urethra, is disposed in the middle of the penis, in a cleft between the undersides of the corpora cavernosa. A "deep artery" runs down the center of each corpus cavernosum and provides blood to sinusoidal spaces in the respective corpus. The end of the penis distal to the body ends in the glans penis which, in uncircumcised males, is protected by the prepuce.

Penile Cancer

As noted in the Background, the National Cancer Institute (NCI) indicates that, when diagnosed early (stage 0, stage I, and stage II), penile cancer is highly curable, but curability decreases sharply for stage III and stage IV. Criteria for staging penile cancer are known in the art. The most common system is the "TNM" (for "tumor, node, metastasis") system of the American Joint Committee on Cancer, set forth at, e.g., Penis: American Joint Committee on Cancer, *AJCC Cancer Staging Manual,* 6th Ed., Springer, NY N.Y., 2002, pp. 302-8. The NCI website notes with regard to stage 0 cancer, that carcinoma in situ of the penis is referred to as erythroplasia of Queyrat when it occurs on the glans, and Bowen's disease when it occurs on the penile shaft. These precursor lesions progress to invasive squamous cell carcinoma in 5% to 15% of cases. The NCI website notes that surgical excision can result in scarring, deformity, and impaired function, and that Mohs micrographic surgery, which involves the excision of successive horizontal layers of tissue with microscopic examination of each layer in frozen section, has been developed for use in patients with in situ and invasive penile cancers. See, e.g., Mobs et al., *J. Urol.* 133(6): 961-6 (1985).

With regard to therapeutic options for stage 1 penile cancer, the NCI website states that, for lesions limited to the foreskin, wide local excision with circumcision may be adequate therapy for control. For infiltrating tumors of the glans, with or without involvement of the adjacent skin, it states that the choice of therapy is dictated by tumor size, extent of infiltration, and degree of tumor destruction of normal tissue. It further states that equivalent therapeutic options include: penile amputation, radiation therapy (i.e., external-beam radiation therapy and brachytherapy), and microscopically controlled surgery. It indicates that, because of the high incidence of microscopic node metastases, elective adjunctive inguinal dissection of clinically uninvolved (negative) lymph nodes in conjunction with amputation is often used for patients with poorly differentiated tumors. Lymphadenectomy, however, can carry substantial morbidity, such as infection, skin necrosis, wound breakdown, chronic edema, and a low, but finite, mortality rate. The NCI indicates that the impact of prophylactic lymphadenectomy on survival is not known.

The NCI states that stage II penile cancer is most frequently managed by penile amputation for local control. Whether the amputation is partial, total, or radical will depend on the extent and location of the neoplasm. External beam radiation therapy and brachytherapy with surgical salvage are alternative approaches.

The NCI site further states that inguinal adenopathy in patients with stage III penile cancer is common but may be the result of infection rather than neoplasm. The website further states that, if palpable enlarged lymph nodes exist 3 or more weeks after removal of the infected primary lesion and completion of a course of antibiotic therapy, bilateral inguinal lymph node dissection should be performed. The methods of the present invention can be performed to assist in dissection of the nodes. Since, in this case, the primary lesion has been removed, the injections are of course made into the cavernous bodies. In cases of proven regional inguinal lymph node metastasis without evidence of distant spread, bilateral ilioinguinal dissection is the treatment of choice. Clinically evident regional lymph node metastasis without evidence of distant spread is an indication for bilateral ilioinguinal lymph node dissection after penile amputation. Radiation therapy may be considered as an alternative to lymph node dissection in patients who are not surgical candidates. Postoperative radiation therapy may decrease incidence of inguinal recurrences.

With respect to stage IV disease, the NCI notes that there is no curative standard treatment. Therapy is directed at palliation, which may be achieved either with surgery or radiation therapy. The standard treatment options include palliative surgery for control of the local penile lesion and palliative radiation therapy for the primary tumor, regional adenopathy, and bone metastases.

Instrumentation

Conveniently, the device used for visualization comprises both a laser and a camera. For convenience of reference, the discussion below refers to the exemplar dye ICG. Persons of skill will recognize that the other dyes mentioned herein as suitable for use in the inventive methods and procedures could be substituted for ICG, with the light source selected or adjusted to provide illumination optimized for the excitation frequency suitable for the particular dye chosen and the device for capturing the light emitted by the dye being selected or adjusted to be able to receive light of the appropriate frequency. For use with ICG, the laser conveniently consists of a laser diode providing a maximum of 3 W output at 806 nm. For other dyes, the laser diode is selected to provide a light with a wavelength at an excitation frequency appropriate for the dye selected.

The laser output is decollimated (i.e. optics are used to spread out the laser light from a tight beam) to provide even illumination over a field of view, for example, 7.6 cm by 7.6 cm at a working distance of 30 cm. The imaging system typically has a camera containing a charge-coupled device ("CCD") or a complementary symmetry metal oxide semiconductor ("CMOS") image sensor sensitive into the near infrared spectrum and, for use with ICG, is equipped with an 815 nm edge filter. In some embodiments, the laser or camera or both, are supported by an articulated arm connected to a wheeled base. This allows the imaging head to be moved into close proximity to the surgical table and for vertical movement of the head to attain an appropriate focal distance above the area of interest. The imaging head and extension arm that protrudes over the surgical field are typically covered with an optically transparent sterile drape. The laser can conveniently be activated by means of a computer command or by foot pedal. Laser/camera devices suitable for intra-operative imaging are commercially available. In some preferred embodiments, the laser/camera device is a SPY® Intra-operative Imaging System, a HELIOS® Imaging System, or a LUNA® Imaging System (all by Novadaq Technologies, Inc., Mississauga, Ontario, Canada).

In some embodiments, an instrument having an optical configuration similar to a fluorescence microscope may be used, in which a dichroic mirror is used to split the paths of the illumination (the excitation light). The excitation light reflects off the surface of the dichroic mirror into the objective, while the fluorescence emission passes through the dichroic mirror to the eyepiece or is converted into a signal to be presented on a screen. The instrument may further have an excitation filter or an emission filter, or both, to select the wavelengths appropriate for each function. Conveniently, the filters are interference filters, which block transmission of frequencies out of their bandpass.

For visualizing the lymph nodes and channels in the area of interest, the ICG is administered by injection into the cavernous bodies, preferably into the crura, permitting the dye to be transported through the lymphatic channels serving the area to the sentinel node or nodes. Following an interval sufficient for the dye to be transported through the channels to the nodes, a 806 nm excitation light causes the dye to fluoresce, emitting light at 830 nm. The emitted light can then be imaged directly or, preferably, is captured using an imaging system. As noted, the capture system is typically a video camera containing a CCD or CMOS image sensor. The capture system feeds the image to a monitor so that the surgeon can visualize the fluorescence of the dye in the lymph nodes in the area of interest in real time. Filters limit the light detected to a range appropriate for the selected fluorescence wavelengths. Optionally, the camera is also attached to a computer and the image is saved, which not only permits documentation of the extent to which the tumor or tumors has spread, but also can be used for training urologic surgeons, nurses, and other medical staff. Typically, the time required for positioning the device is 2 minutes, while the total time that the vessels are illuminated with laser light is 30 seconds.

The methods described herein are suitable for use in mammals. Examples of suitable mammals include, but are not limited to, humans, non-human primates, dogs, cats, sheep, cows, pigs, horses, mice, rats, rabbits, and guinea pigs. Use in humans is primates, and particularly in humans, is preferred.

Dyes for Imaging

As persons of skill are aware, fluorescent dyes have a particular excitation wavelength which causes the dye to fluoresce and emit light of a particular emission wavelength. Persons of skill will appreciate that a considerable literature is available in the art on the characteristics of different dyes, including their excitation wavelength and emission wavelength. This literature is well known, and will not be set forth in detail herein.

The dye is imaged by exciting it with a light that has an excitation wavelength appropriate for the particular dye used. Persons of skill are aware that a variety of dyes exist, and that each dye has an excitation wavelength and an emission wavelength. Some dyes, for example, fluoresce under ultraviolet ("UC") illumination while others fluoresce under incandescent illumination. The literature on the use of fluorescent dyes and probes in biological assays includes, for example, Dewey, T. G., Ed., Biophysical and Biochemical Aspects of Fluorescence Spectroscopy, Plenum Publishing (1991), Guilbault, G. G., Ed., Practical Fluorescence, Second Edition, Marcel Dekker (1990), Lakowicz, J. R., Ed., Topics in Fluorescence Spectroscopy: Techniques (Volume 1, 1991); Principles (Volume 2, 1991); Biochemical Applications (Volume 3, 1992); Probe Design and Chemical Sensing (Volume 4, 1994); Nonlinear and Two-Photon Induced Fluorescence (Volume 5, 1997); Protein Fluorescence (Volume 6, 2000); DNA Technology (Volume 7, 2003); Plenum Publishing, and Lakowicz, J. R., Principles of Fluorescence Spectroscopy, Second Edition, Plenum Publishing (1999) and W. T. Mason, ed., Fluorescent and Luminescent Probes for Biological Activity. A Practical Guide to Technology for Quantitative Real-Time Analysis, Academic Press (Second Ed., 1999).

Preferably, the dye selected is one that has low toxicity and has excitation and emission peaks within the "optical window" of tissue, where absorption due to endogenous chromophores is low. Preferred fluorescent dyes suitable for use in the methods of the invention are non-toxic dyes which fluoresce when exposed to radiant energy, e.g. light. Preferably, the dyes are near infrared fluorochromes, or "NIRF" that emit light in the near infra red spectrum. Near infrared light can penetrate tissue to a depth of several millimeters to a few centimeters. In some embodiments, the dye is a tricarbocyanine dye, and in particularly preferred embodiments, is ICG. In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The dyes may be mixed or combined. In some embodiments, dye analogs may be used. A "dye analog" is a dye that has been chemically modified, but still retains its ability to fluoresce when exposed to radiant energy of an appropriate wavelength.

ICG, Fast Blue and Fluorogold have all been used in mammals with low evidence of toxicity and are preferred. As noted, ICG is particularly preferred both because it has low toxicity and because it has been approved by the Food and Drug Administration for several diagnostic purposes in humans. Further, its absorption (excitation) and emission peaks (805 and 835 nm, respectively) lie within the "optical window" of tissue. ICG is commercially available from, for example, Akorn, Inc. (Buffalo Grove, Ill.), which sells it under the name IC-GREEN™. After intravenous injection, ICG is bound within 1 to 2 seconds, mainly to globulins (1-lipoproteins), and remains intravascular, with normal vascular permeability. ICG is not metabolized in the body and is excreted exclusively by the liver, with a plasma half-life of 3 to 4 minutes. It is not reabsorbed from the intestine and does not undergo enterohepatic recirculation. The recommended dose for ICG video angiography is 0.2 to 0.5 mg/kg; the maximum daily dose should not exceed 5 mg/kg.

For intraoperatively visualizing the lymph nodes and channels, the surgical field, or the portion of the surgical field in which imaging is desired, is illuminated with a light of the excitation wavelength or wavelengths suitable for the dye or dyes used. Since the channels are thin and the nodes are small (accounting in part for the difficulty in discerning them with the unaided eye), ambient light may need to be dimmed to permit the fluorescence to be seen. Observation will typically also require magnification. Where the excitation wavelength is outside of the visible range (where, for example, the excitation wavelength is in the ultraviolet or near infrared range), the light source may be designed to permit switching or "toggling" between the excitation wavelength and visible light. This permits the practitioner to note the position of the node or nodes using the fluorescent property in relation to the rest of the surgical field and surrounding (but non-fluorescent) structures.

In some embodiments, an instrument having an optical configuration similar to a fluorescence microscope may be used, in which a dichroic mirror is used to split the paths of the illumination (the excitation light). The excitation light reflects off the surface of the dichroic mirror into the objective, while the fluorescence emission passes through the dichroic mirror to the eyepiece or is converted into a signal to be presented on a screen. The instrument may further have an excitation filter or an emission filter, or both, to select the wavelengths appropriate for each function. Conveniently, the filters are interference filters, which block transmission of frequencies out of their bandpass.

The dye is typically administered by an injection into one or both of the corpora cavernosa. Typically, the dye will be administered some hours preoperatively, to permit the dye to be transported to the nodes in the area of interest prior to commencing the surgical operation.

Conveniently, the dye may be administered in the patient's room. Typically, the dye is administered sufficiently before the intended surgery to permit the dye to flow to the sentinel nodes draining the tumor area, but not so long before the surgery that the dye has been cleared from the nodes. Since the nodes could be detected through the body wall of the animals from 2 hours to 7 days after injection, it appears that the dye can be administered at the convenience of the patient and the practitioner from 2 hours up to a week before the intended surgery. Typically, however, a patient presenting with penile cancer will be injected with the dye no more than a few days before surgery is contemplated, since delay in performing the surgery will rarely be to the patient's benefit. Typically, therefore, the dye is administered at least about 2 hours but not more than 72 hours before the intended surgery. In some embodiments, the dye is administered at least about 2 hours but not more than 48 hours before the intended surgery. In other embodiments, the dye is administered at least about 2 hours but not more than 36 hours before the intended surgery. In preferred embodiments, the dye is administered between about 2 hours to 24 hours before the intended surgery. In still preferred embodiments, the dye is administered between about 2 hours to about 14 hours before the intended surgery, with "about" meaning a half hour on either side. Whether the patient has been injected too recently to provide adequate time for the dye to drain to the lymph nodes (for example, a half hour after injection, the dye would not yet be expected to have drained sufficiently to the nodes for optimal detection) can be readily determined pre-operatively by simply illuminating the groin with near infrared illumination under conditions permitting detecting any light emitted by the dye. If fluorescence is not sufficient to permit visualization of the nodes in the groin, a technician can simply reilluminate the area at half hour intervals or such other intervals as may be convenient until sufficient dye has drained to the sentinel lymph nodes to permit ready visualization.

The maximum daily dosage of ICG for adults is 2 mg/kg. There is no data available describing the signs, symptoms, or laboratory findings accompanying an overdose of ICG. The $LD_{50}$ after IV administration ranges between 60 and 80 mg/kg in mice, 50 and 70 mg/kg in rats, and 50 to 80 mg/kg in rabbits.

EXAMPLES

Example 1

Intraoperative video angiography is performed with a laser-fluorescence imaging device (Novadaq Technologies, Inc., Mississauga, Ontario, Canada) consisting of a near infrared (NIR) laser light source and a NIR-sensitive digital camcorder. For measurements, the unit is positioned 30 to 40 cm from the area of interest. ICG, dissolved in water, is then injected as a bolus. The NIR light emitted by the laser light source induces ICG fluorescence. The fluorescence is recorded by a digital video camera, with optical filtering to block ambient and laser light so that, when desired, only ICG fluorescence is captured. Images can be observed on screen in real time (25-30 images/sec). The images can be reviewed and stored on the digital video camera or transferred to a computer or to storage media.

Example 2

Sprague-Dawley rats, 60 to 100 days old, weighing 275-325 grams are used. All animals are anesthetized using intraperitoneal injection of Ketamine/Xylazine (40-80 mg/kg and 5/10 mg/kg, respectively) or isoflurane. No pre-anesthetic medications are used. When appropriate depth of anesthesia is reached, positioning of the animal takes place. All animals are fastened to a padded and heated restraint device in the supine position using gauze knots to fix all four extremities. Depth of anesthesia, regularity of respirations, and heart beat palpation are repeatedly checked. A pulse oximeter may be used to monitor the animal. Placebo (distilled water) or fluorochromes, ICG or Fluorogold, is administered by intra-penile, sub-albugineal injection of 25 ul of ICG diluted in 100 µl of water for injection, per cavernous body.

Surgery/Procedure starts after appropriate preparation of surgical field by Povidone-Iodine scrub, 70% Isopropyl Alcohol and Povidone-Iodine solution. The surgical field includes the genital area, lower abdomen and perineum. The penis is squeezed out from the prepuce, then stretched using finger grip of the glans until maximally stretched; a clamp used for atraumatic clamping in neurosurgical operation on brain aneurysms is then placed at the root of the penis. This allows blood to pool inside the cavernous bodies, producing an erection and permitting easier application of a 27 Gauge butterfly needle to both sub-albugineal spaces. Adequate placement is assured when blood is easily aspirated. 0.5 mg/kg of ICG and 1 mg/kg of Fluorogold diluted in distilled water to total volume of 50 µl is injected, 25 µl per cavernous body. A placebo group is injected using 25 µl of distilled water per cavernous body. Animals in all groups have an exploratory laparotomy through midline lower incision, with intraoperative identification of nodes draining the penis. Midline incisions are made from umbilicus to pubis. Bowels and testicles after their release from scrotal attachments are packed back to upper abdomen. For better visualization of the pelvic structures, surgical loupes with 3.8× magnification are used. After release of the clamps, the 27 Gauge needles are removed, but slight finger pressure at the injection sites is maintained for 3-5 minutes to prevent extravasation. Buprenorphine (0.01-0.05 mg/kg) is administered intraoperatively and then as needed to control pain.

Post-procedurally, optimal recovery is routinely performed in all animals: animals are kept warm using warming packs, pads and lamps, the animals are placed on a paper towel, and are rotated from side to side every 15 minutes until they are able to maintain sternal recumbence. 3-4 ml of Lactated Ringer solution, warmed to 37° C., is administered subcutaneously and unilaterally in the flank region, preventing postoperative dehydration of the animal. Animals are attended at all times during postoperative recovery. The animals are then returned to their home cages, and hydration is assessed on a daily basis. Analgesia is used for all animals for postoperative pain. Animals are checked for signs of pain every 6 hours during first 24 hours post-surgery and then every 12 hours until euthanasia. Signs of acute pain are guarding (protecting the painful area), vocalization, especially when the animal moves or the painful area is touched, licking, biting, scratching or shaking a particular area, pacing, lack of mobility as seen with joint, colic or gut pain or an unusual gait posture during movement, failure to groom, causing an unkempt appearance, abnormal resting postures, loss of appetite or reduction in water consumption, and changes in behavior or signs of aggression.

To perform harvesting of lymph nodes, the rats undergo a second surgery (non-survival) and postmortem harvesting at chosen timepoints after fluorochrome injection.

Anesthesia identical to the first procedure is administered and then appropriate skin preparation for surgery is performed. The same level of incision is used in second surgery/harvesting procedure. The bladder and prostate are exposed as in the first surgery. The penis is denuded of skin and the prepuce circumcised. The animal is euthanized by cardiac exsanguination. Death of the animal is confirmed using pulse oximeter and observation of complete absence of heart contractions.

Example 3

Twenty two 22 male Sprague-Dawley rats received penile intracavernous ICG injections (20 μl of 0.25 mg/ml). From 2 hours to 7 days later, near infrared fluorescence (NIRF) imaging was performed both before and during dissection. Control rats received comparable saline injections at several time points. A Novadaq intraoperative NIRF imaging system (SPY®) was used for macroscopic fluorescence imaging and an Olympus NIRF microscope IX 70 (Olympus America, Inc., Center Valley, Pa.) was used for histology. All animals were anesthetized and shaved before imaging. All visualized nodes were sent for NIR microscopy and haematoxylin and eosin (H&E) staining for histological examination.

Example 4

Inguinal lymph node NIRF was detected through the body wall from 2 hours to 7 days after ICG injection (FIG. 1). More than one pair of sentinel lymph nodes were visualized in 2 rats. No fluorescence was seen in controls. Intraoperative observations confirmed preoperative localization of all inguinal nodes (FIG. 2). Inguinal and iliac sentinel lymph nodes were clearly visualized with NIRF, and were difficult to visualize otherwise. Lymphatic channels were seen leading to sentinel lymph nodes at 6, 12 and 24 hours (FIG. 1). Lymphatic channels leading to the sentinel lymph nodes were seen in animals examined at 6, 12, and 24 hours post-injection of ICG. (FIG. 1). All lymph nodes were confirmed by NIR microscopy and by conventional histology. Thus, NIR fluorescence using ICG facilitates both pre- and intraoperative identification of the first site of penile lymphatic drainage. The methods of the invention should therefore improve the accuracy of surgical staging in patients with penile carcinomas.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of localizing before or during a surgical operation a lymph node draining a penile tumor having edges and a base, in a subject, comprising:
   a) 1 hour to 6 hours prior to said surgical operation, injecting the edges or the base of said tumor of said subject with 30 to 300 μL of a dye which fluoresces at an emission wavelength when said dye is contacted with an excitation wavelength;
   b) exposing said lymph node before or during said operation to illumination using a laparoscopic instrument, the illumination comprises said excitation wavelength and causes said fluorescent dye to fluoresce; and,
   c) detecting the fluorescence of said dye at said lymph node.

2. The method of claim 1, wherein said lymph node is a sentinel lymph node.

3. The method of claim 1, wherein said dye is injected into the edges of said tumor.

4. The method of claim 1, wherein said dye is injected into the base of said tumor.

5. The method of claim 1, wherein said lymph node is visualized on an image display.

6. The method of claim 1 wherein said dye is a dye which fluoresces when exposed to near infrared light.

7. The method of claim 1, wherein said dye is a tricarbocyanine dye.

8. The method of claim 7, wherein the tricarbocyanine dye is indocyanine green.

9. The method of claim 1, wherein the subject is a human.

10. The method of claim 1, wherein said dye is injected between 1 hour and 3 hours before said surgical operation.

11. The method of claim 1, wherein said dye is injected between 1 hour and 2 hours before said surgical operation.

12. The method of claim 1, wherein said steps (b) and (c) are performed during said operation.

13. The method of claim 1, wherein said operation is a laparoscopic operation.

14. The method of claim 1, wherein step (a) requires two to five injections.

* * * * *